United States Patent [19]
Aderem et al.

[11] Patent Number: 5,885,772
[45] Date of Patent: Mar. 23, 1999

[54] METHOD FOR THE DETECTION OF ANENCEPHALY

[75] Inventors: Alan A. Aderem; Jianmin Chen; Sandy Chang, all of New York, N.Y.

[73] Assignee: The Rockefeller University, New York, N.Y.

[21] Appl. No.: 405,175

[22] Filed: Mar. 16, 1995

[51] Int. Cl.$^6$ .............................. C12Q 1/68; C12P 19/34; C07H 21/02; C07H 21/04
[52] U.S. Cl. ........................... 435/6; 435/91.2; 536/23.1; 536/24.33; 536/24.3; 800/2
[58] Field of Search ..................... 435/6, 91.2; 536/23.1, 536/24.33, 24.3; 800/2

[56] References Cited

PUBLICATIONS

Kim et al (1994) J. Biol. Chem. 269:28214–28219.
Li et al (1992) Cell 70:791–801.
Erusalimsky et al (1991) J. Biol. Chem. 266:7073–7080.
Harlan et al (1991) J. Biol. Chem. 266:14399–14405.
Joshi et al (1991) J. Cell Biol. 115:665–675.
Seykora et al (1991) Proc. Natl. Acad. Sci. USA 88:2505–2509.
Liu et al (1990) Trends Pharmacol. Sci. 11:107–111.
Stumpo et al (1989) Proc. Natl. Acad. Sci. USA 86:4012–4016.
Graff et al (1989) Mol. Endocrinol. 3:1903–1906.
Aderem, A. (1992) Cell 71:713–716.
Rosen et al. (1990) J. Exp. Med. 172:1211–1215.
Thelen et al. (1991) Nature 351:320–322.
Hartwig et al. (1992) Nature 356:618–622.
Aderem, A. (1988) Nature 332, No. 6212:362–364.
Thelen et al. (1990) Proc. Natl. Acad. Sci. USA 87:5603–5607.
Aderem et al. (1986) Natl. Acad. Sci. USA 83:5817–5821.
Myat et al. (Abstract No. 1716) Cell Motility II: 295a.
Aderem, A. (1992) TIBS 17:438–443.

*Primary Examiner*—W. Gary Jones
*Assistant Examiner*—Dianne Rees
*Attorney, Agent, or Firm*—Klauber & Jackson

[57] ABSTRACT

The invention includes methods and materials, including probes, to be used as diagnostic tools for detecting anencephaly. Such methods may be practiced by both manual and automated means, and in the instance of the latter, suitable equipment for such automated performance is also contemplated. Also included within the invention are mouse embryos null for a gene encoding a protein kinase C substrate which binds calcium-calmodulin and regulates cell movement and membrane traffic, and cells derived from such embryos.

14 Claims, 15 Drawing Sheets

FIG.1A

```
1    GCTTTAGAGAGCGGGCAGCGGGCGGGCCGTAGCGGGTCGGCCCGAGCGGGGTGC
61   AGCTCGGTTTCCCCGACACCTCCCCTGCGCTCAGCGCTCCCCACCCCTCTGCGGGC
121  CGGGCCGACCCACCGAACTATCCCTGGGCGCGAGCCCGGCGCTCCGGGCGCCCCAA
181  CAGACCCCCCACCATGGGCCAGAGCTCCAAGGCTCCAAGGCTCCCGGGCGACGTGACCGCC
                    M  G  Q  S  S  K  A  P  R  G  D  V  T  A
241  GAGGAGGCAGCAGGCGCTTCCCCGCGAAGGCCAACGGACAGGAGAATGGCCACGTGAAA
     E  E  A  A  G  A  S  P  A  K  A  N  G  Q  E  N  G  H  V  K
301  AGCAATGGAGACTTAACCCCAAGGGTGAAGGGGAGTCGCCCGTGAACGGAACAGAT
     S  N  G  D  L  T  P  K  G  E  G  E  S  P  P  V  N  G  T  D
361  GAGGCAGCTGGGGCCACTGGGCGATGCAGCCAGAGCCACCCCTAGCCAGGCCGCCGAG
     E  A  A  G  A  T  G  D  A  I  E  P  A  P  P  S  Q  G  A  E
421  GCCAAGGGGACACCCCCCCCAAGAAGAAGAAATTCTCTTTCAAG
     A  K  G  D  A  P  P  K  E  T  P  K  K  K  K  F  S  F  K
481  AAGCCTTTCAAATTGAGCGGCCTGTCCTTCAAGAGAAGAATCGAAGGCAGGGGCGAC
     K  P  F  K  L  S  G  L  S  F  K  R  N  R  K  E  G  G  G  D
541  TCCTCTGCCTCCCCCCCACGGGAGGAAGAGCAGGAGATCGGTGCCTGCAGC
     S  S  A  S  S  P  T  E  E  E  Q  E  Q  E  I  G  A  C  S
601  GAAGAGGGCACTGCCCCGGAGGGCAAGGCCGCTGCCAAGAGAGCACAGAGAGCCCCAG
     E  E  G  T  A  P  E  G  K  A  A  T  P  E  S  Q  E  P  Q
661  GCCAAGGGGGCAGAGGCTGGCGTCCACTCCCTCGGGCAAGAGGAGGCAGGG
     A  K  G  A  E  A  G  A  C  K  G  G  D  T  E  E  A  G
721  CCCCCAGCCGAGCCGAGTACTCCGGAGAGTGCCCTACACGCCGGCGCC
     P  P  A  E  P  S  T  P  S  G  P  E  S  G  P  T  P  A  G  A
781  GAGCAGAATGAGTAGTAGCTGATCTCTTAAGCTACAAAACTGT
     E  Q  N  E
```

FIG.1B

```
 841 GCTGTCCTTGTGAGGTCACTGCCTGCCCCTGTGCCCTGGCCTGCCTTCCTGTGCCCAGAA
 901 AGGAGGGGCTGCTGCGCTCCAACCACTTCCCTCCTCCTCCTCCTGTGGATTCTCC
 961 CATCAGCCATCTGGTCTTCCTCGCAAGGCCAGTGCCCTTACATTTCCCAA
1021 GTTAGGTTAGTGATGTGAAATGCTCCTGGTCCCAGCCCCCCTGACCCCCACCCCT
1081 GCCCTGCAAGGCAATTGCTGGTTCTCCCTCGGTTCTCTTTCCAAGTAGGTTCTGTTT
1141 ACCCTACTCCCCAAATCCCTGAGCCAGAAGTGGGGTGCTTATCCCCAAACCCTGAGTG
1201 TCCAGCCCTTCCCCTGTTGAGTTTTTAGTCTCTTGTGCCTAGTGGCCACCTGGGCTG
1261 GGGAGGACACTGCCCCTGTCTCTGGTTTTATAAATGTCTTACTCAAGTTCAAACCTCCAG
1321 CTTGTGAATCAACTGTGTCTCTTTTTGACTTGGTAAGCAAGTATTAGGCTTTGGGGTG
1381 GGGGAAGTCTGTAATGTGAAACAACTTCTTGTTCTTTTTCTCCCATTGTTGTAAATAA
1441 CTTTTAATGGCCAAACCCCAGATTTGTACTTTTTTTCTAATTGCTAAAACCATTCTCT
1501 TCCACCTGGTTTTACTGTAACCTTTGGAAAAGGAATAAATGTTGTCCCTTTAAAAAAAA
1561 AAAAAA
```

FIG.1C

```
Rabbit   - MGSQSSKAPRGDVTAEEAAGASPAKANGQENGHVKSNGDLTPKGEGESPP    -50
           ::::::::::::::::::::::::::::::::::: :::::::::::::::
Murine   - MGSQSSKAPRGDVTAEEAAGASPAKANGQENGHVRSNGDLTPKGEGESPP    -50

Rabbit   - VNGTDEAAGATGDAIEPAPPSQGAEAKGDAPPKETPKKKKKFSFKKPFKL    -100
           :::::::::::::::::::: :::  :: ::::::::::::::::::::
Murine   - VNGTDEAAGATGDAIEPAPPSQEAEAKGEVAPKETPKKKKKFSFKKPFKL    -100

Rabbit   - SGLSFKRNRKEGGGDSSASSPTEEEQEQGEIGACSEEGTAPEGKAAATPE    -150
           :::::::::::::::::::::::::::::: :::  :: :::::::::
Murine   - SGLSFKRNRKEGGGDSSASSPTEEEQEQGEMSACSDEGTAQEGKAAATPE    -150

Rabbit   - SQEPQAKGAEAGAACKGGDTEEEAGPPA-EPSTPSGPESGPTPAGAEQNE    -199
           ::::::::::: ::: :::::::::::  :::::::::::::: :::::
Murine   - SQEPQAKGAEASAASKEGDTEEEAGPQAAEPSTPSGPESGPTPASAEQNE    -200
```

FIG. 2A

```
                                            MH2 DOMAIN
HumanM      -MGAQFSKTAAKGEAAAERPGEAAVASSPSKANGQENGHVKVNGDASPAAAESGAKEELQANGSAPAADKEEPAAAGSGAASPSAAEKGEPAAAAAPEAGA   100
BovineM     -MGAQFSKTAAKGEATAERPGEAAVASSPSKANGQENGHVKVNGDASPAAAEPGAKEELQANGSAPAADKEEPAAAGSGAASPAAAEKDEPAAAA-PDACA    99
MurineM     -MGAQFSKTAAKGEATAERPGEAAVASSPBKANGQENGHVKVNGDASPAAAEPGAKEELQANGSAPAADKEEPASGS--AATPAAAEKDEAAAATEP--GA    96
RatM        -MGAQFSKTAAKGEAAAERPGEAAVASSPSKANGQENGHVKVNGDASPAAAEPGAKEELQANGSAPAADKEEPASGG--AATPAAADKDEAAAAPEP--GA    96
ChickenM    -MGAQFSKTAAKGEAAAEXPGEA-VAABPSKANGQENGHVKVNGDASPAAAEAG-KEEVQANGSAPAEE-----------TGKEEAASSEP-------    77
Rabbit42K   -MGAQFSKTAAKGEAAAEXPGEA---EAAGA-BPAKANGQENGHVKVSNGDLTP----------------------------KGEGES---------PPVNGTDEAAGAT----GD  63
Murine42K   -MGSQSSK-APRGDVTAE---EAAGA-SPAKANGQENGHVRSNGDLTP--------------------------KGEGES---------PPVNGTDEAAGAT----GD  63
             *******  ** ****  *                *****                                                                   *

EFFECTOR DOMAIN
HumanM      -SPVEKEAPAEGEAAEPGSPTAAEGEAASAASSTSSPKAEDGATPSPSNETPKKKKRFSFKKSFKLSGFSFKKNKCEAGEGEAEAPA---AEGGKDEAA   197
BovineM     -SPVEKEAPVEGEAAEPGSPTAAEGEAASAASSTSSPKAEDGATPSPSNETPKKKKRFSFKKSFKLSGFSFKKNKCEGGEAEGAAGAS AEGGKDEAS    199
MurineM     -GAADKEAA-EAEPAEPSSP-AAEAEGASA-SSTSSPKAEDGAAPSPSSETPKKKKRFSFKKSFKL&GFBFKKSKKESGEGAEAE---GATAEGAKDEAA   190
MurinH      -ATADKEAA-EAEPAEPGSP-SAETEGASA-SSTSSPKAEDGAAPSPSSETPKKKKRFSFKKSFKLSGFSFKKNKEACEAESGGAAAAAAEGGKEEAA   190
RatM        -AS-EKEAA-EAESTEPASPAEGEA----------SPKTEEGATPSSSSETPKKKKRFSFKPKKK-FSFKQFFKLSGLSFKRNREGGDSSASSPTEE---   165
ChickenM    -AI-------EPAPP-SQGAEAKGDA----------------PPKETPKKKK-FSFKPFKKK-FSFKQFFKLSGLSFKRNRKCGGDSSASSPTEE---   124
Rabbit42K   -AI-------EPAPP-SQGAEAKGEV----------------APKETPKKKKK-FSFKQPFKLSGLSFKRNRKGGGDSSASSPTEE---   124
Murine42K                                                                                         *********  *** ***  *

HumanM      -GGAAAAAEACAASGEQAAAPGEEAAAGEEGAAGGDSQEAKPQEAAVAPEXP--PASDEYKAAEPSKVEEKKAEEA--GASAAACEAPSAAGLVCPRRG   293
BovineM     -GGAAAAAGEAGAAPGEPTAAPGEEAAAGEEGAAGGDPQEAKPEEAAVAPEXP--PARRGAKAVEEPSKAEEKKAEEAG-VSAAGAAGCEAPSAAGPCPRAG   297
MurineM     ----AAGGEGAAPGEQAGG--------AGAEGAAGGEPREAEAAEPE-QPEQPEQPAAEPQAEEQSEAAGEKAEE---PAPGATAGDASSAAG----PEQE   274
RatM        ----AAGGEGAAPGEQAGG--------AGAEGAEGGESREAEAAEPE-QPEQPEQPAAEPQAEEPSEAVGEKAEE---PAPGATADDAPSAAG----PEQE   274
Chicken     ----AAGGDAAAPGEQAGQ---------QEAPSESSPEGP---AEPAE AGAEGAEGGESREAEAAEPEPRAEEPSEAVGEKAEE---PAPGATADDAPSAAG----EQE   253
Rabbit42K   ----AAAPEAAG-------GEEGKAAAEEASA---AAAGSREAAKEEAGDSQEAKSDEAAPEKATGEEAPAAEEQQQQQEKAAEEAGAAATSEACSG---EEE   173
Murine42K   ----AAAPEAAG-------EQEQGEIGACSEEGTAPEGKAAAT-----------PESQEPQAK-------------------------------EEE   173
                                                                                                              *

HumanM      -GSPRGCARGRRSLNQACAAPSQEAQPECSPEAP--PAEAAE   332
BovineM     -GAPREEAAPPRA-SSACSAPSQEAQPECSPEAP--PAEAAE   335
MurineM     -APAATDEAA---ASAAPAASPEPQPECSPEAP--PAPTAE   309
RatM        -APAATDEPA----ASAAPSASPEPQPECSPEAP--PAPVAE   309
Chicken     -AAPAEPAAAR-------QEAPSESSPEGP---AEPAE    281
Rabbit42K   -AGPP-AEPSTPSGP-----------------ESGPTPAGAEQNE   199
Murine42K   -AGPQAAEPSTPSGP-----------------ESGPTPASAEQNE   200
             *
```

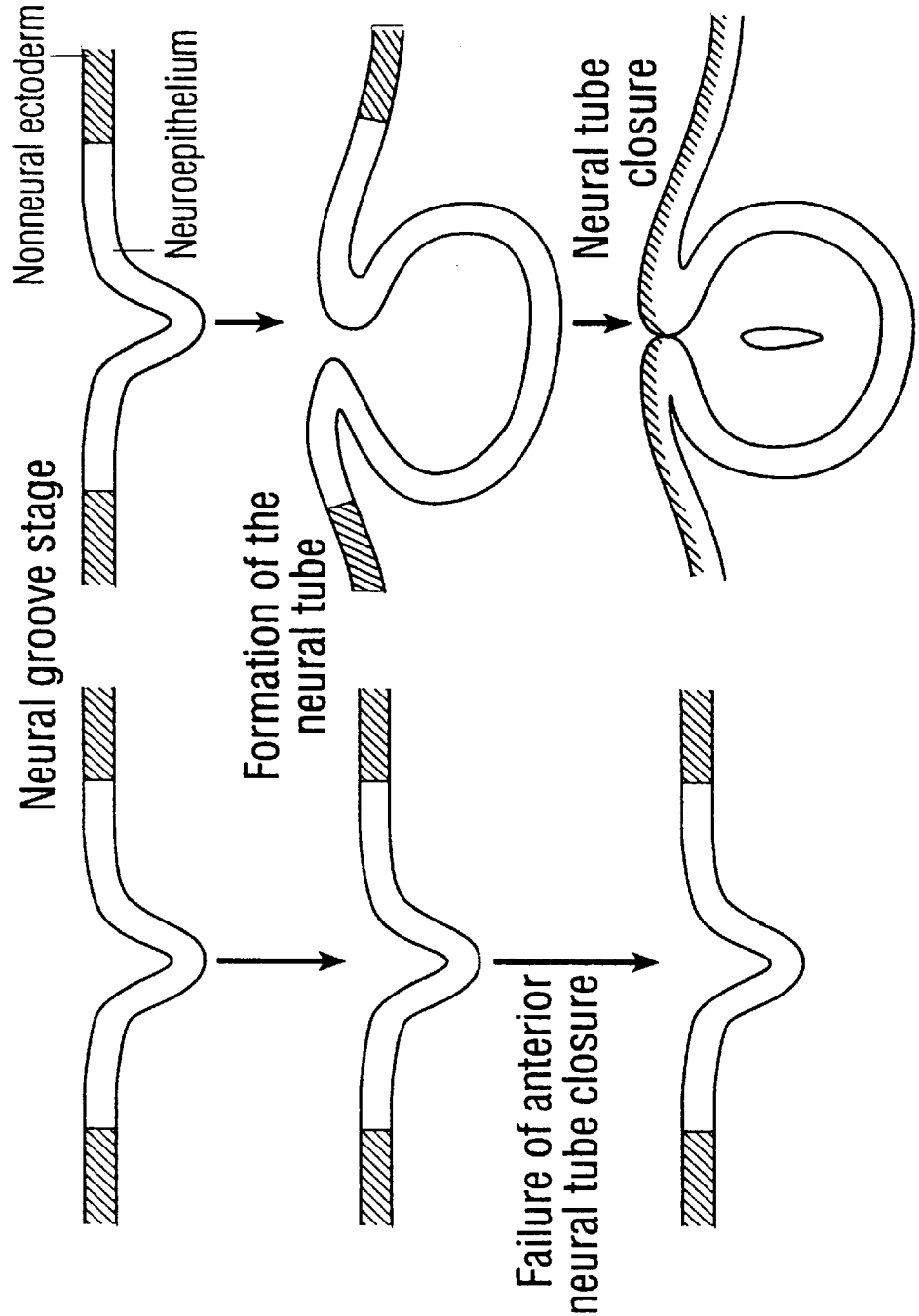

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: phosphopeptide of MARCKS ( i i i ) HYPOTHETICAL: NO ( v ) FRAGMENT TYPE: internal ( x i ) SEQUENCE DESCRIPTION: SEQ ID NO:1:

Phe   Lys   Lys   Ser
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: phosphopeptide of MacMARCKS ( i i i ) HYPOTHETICAL: NO ( v ) FRAGMENT TYPE: internal ( x i ) SEQUENCE DESCRIPTION: SEQ ID NO:2:

Phe   Lys   Lys   Pro (2) INFORMATION FOR SEQ ID NO:3:

(i) SEQUENCE CHARACTERISTICS:
        (A) LENGTH: 199 amino acids
        (B) TYPE: amino acid
        (D) TOPOLOGY: linear (ii) MOLECULE TYPE: protein
        (A) DESCRIPTION: rabbit alveolar macrophage MacMARCKS (xi) SEQUENCE DESCRIPTION: SEQ ID NO:3:

```
Met Gly Ser Gln Ser Ser Lys Ala Pro Arg Gly Asp Val Thr Ala Glu
 1               5                  10                  15
Glu Ala Ala Gly Ala Ser Pro Ala Lys Ala Asn Gly Gln Glu Asn Gly
            20                  25                  30
His Val Lys Ser Asn Gly Asp Leu Thr Pro Lys Gly Glu Gly Glu Ser
        35                  40                  45
Pro Pro Val Asn Gly Thr Asp Glu Ala Ala Gly Ala Thr Gly Asp Ala
    50                  55                  60
Ile Glu Pro Ala Pro Pro Ser Gln Gly Ala Glu Ala Lys Gly Asp Ala
65                  70                  75                  80
Pro Pro Lys Glu Thr Pro Asn Ala Lys Lys Lys Phe Ser Phe Lys
                85                  90                  95
Pro Phe Lys Leu Ser Gly Leu Ser Phe Lys Arg Asn Arg Lys Glu Gly
                100                 105                 110
Gly Gly Asp Ser Ser Ala Ser Ser Pro Thr Glu Glu Glu Gln Glu Gln
            115                 120                 125
Gly Glu Ile Gly Ala Cys Ser Glu Glu Gly Thr Ala Pro Glu Gly Lys
    130                 135                 140
Ala Ala Ala Thr Pro Glu Ser Gln Glu Pro Gln Ala Lys Gly Ala Glu
145                 150                 155                 160
Ala Gly Ala Ala Cys Lys Gly Gly Asp Thr Glu Glu Glu Ala Gly Pro
                165                 170                 175
Pro Ala Glu Pro Ser Thr Pro Ser Gly Pro Glu Ser Gly Pro Thr Pro
            180                 185                 190
Ala Gly Ala Glu Gln Asn Glu
            195
```

(2) INFORMATION FOR SEQ ID NO:4:

(i) SEQUENCE CHARACTERISTICS:
        (A) LENGTH: 200 amino acids
        (B) TYPE: amino acid
        (D) TOPOLOGY: linear (ii) MOLECULE TYPE: protein
        (A) DESCRIPTION: murine resident peritoneal macrophage
            MacMARCKS (xi) SEQUENCE DESCRIPTION: SEQ ID NO:4:

```
Met Gly Ser Gln Ser Ser Lys Ala Pro Arg Gly Asp Val Thr Ala Glu
 1               5                  10                  15
Glu Ala Ala Gly Ala Ser Pro Ala Lys Ala Asn Gly Gln Glu Asn Gly
            20                  25                  30
His Val Arg Ser Asn Gly Asp Leu Thr Pro Lys Gly Glu Gly Glu Ser
        35                  40                  45
Pro Pro Val Asn Gly Thr Asp Glu Ala Ala Gly Ala Thr Gly Asp Ala
    50                  55                  60
```

```
Ile  Glu  Pro  Ala  Pro  Pro  Ser  Gln  Glu  Ala  Glu  Ala  Lys  Gly  Glu  Val
65                       70                  75                       80

Ala  Pro  Lys  Glu  Thr  Pro  Asn  Ala  Lys  Lys  Lys  Lys  Phe  Ser  Phe  Lys
                    85                  90                       95

Pro  Phe  Lys  Leu  Ser  Gly  Leu  Ser  Phe  Lys  Arg  Asn  Arg  Lys  Glu  Gly
               100                      105                      110

Gly  Gly  Asp  Ser  Ser  Ala  Ser  Ser  Pro  Thr  Glu  Glu  Gln  Glu  Gln
          115                      120                      125

Gly  Glu  Met  Ser  Ala  Cys  Ser  Asp  Glu  Gly  Thr  Ala  Gln  Glu  Gly  Lys
          130                 135                      140

Ala  Ala  Ala  Thr  Pro  Glu  Ser  Gln  Glu  Pro  Gln  Ala  Lys  Gly  Ala  Glu
145                      150                 155                           160

Ala  Ser  Ala  Ala  Ser  Lys  Glu  Gly  Asp  Thr  Glu  Glu  Glu  Ala  Gly  Pro
                    165                      170                      175

Gln  Ala  Ala  Glu  Pro  Ser  Thr  Pro  Ser  Gly  Pro  Glu  Ser  Gly  Pro  Thr
               180                      185                      190

Pro  Ala  Ser  Ala  Glu  Gln  Asn  Glu
               195                      200
```

(2) INFORMATION FOR SEQ ID NO:5:

(i) SEQUENCE CHARACTERISTICS:
    (A) LENGTH: 332 amino acids
    (B) TYPE: amino acid
    (C) STRANDEDNESS: single
    (D) TOPOLOGY: linear (ii) MOLECULE TYPE: protein
    (A) DESCRIPTION: predicted primary structure of human MARCKS (iii) HYPOTHETICAL: NO (xi) SEQUENCE DESCRIPTION: SEQ ID NO:5:

```
Met  Gly  Ala  Gln  Phe  Ser  Lys  Thr  Ala  Ala  Lys  Gly  Glu  Ala  Ala  Ala
1                   5                        10                       15

Glu  Arg  Pro  Gly  Glu  Ala  Ala  Val  Ala  Ser  Ser  Pro  Ser  Lys  Ala  Asn
               20                  25                       30

Gly  Gln  Glu  Asn  Gly  His  Val  Lys  Val  Asn  Gly  Asp  Ala  Ser  Pro  Ala
          35                  40                       45

Ala  Ala  Glu  Ser  Gly  Ala  Lys  Glu  Glu  Leu  Gln  Ala  Asn  Gly  Ser  Ala
     50                      55                      60

Pro  Ala  Ala  Asp  Lys  Glu  Glu  Pro  Ala  Ala  Ala  Gly  Ser  Gly  Ala  Ala
65                       70                       75                       80

Ser  Pro  Ala  Ala  Ala  Glu  Lys  Gly  Glu  Pro  Ala  Ala  Ala  Ala  Ala  Pro
                    85                  90                       95

Glu  Ala  Gly  Ala  Ser  Pro  Val  Glu  Lys  Glu  Ala  Pro  Ala  Glu  Gly  Glu
               100                 105                      110

Ala  Ala  Glu  Pro  Gly  Ser  Pro  Thr  Ala  Ala  Glu  Gly  Glu  Ala  Ala  Ser
          115                      120                      125

Ala  Ala  Ser  Ser  Thr  Ser  Ser  Pro  Lys  Ala  Glu  Asp  Gly  Ala  Thr  Pro
          130                      135                      140

Ser  Pro  Ser  Asn  Glu  Thr  Pro  Lys  Lys  Lys  Lys  Lys  Arg  Phe  Ser  Phe
145                      150                      155                      160

Lys  Lys  Ser  Phe  Lys  Leu  Ser  Gly  Phe  Ser  Phe  Lys  Lys  Asn  Lys  Lys
                    165                      170                      175

Glu  Ala  Gly  Glu  Gly  Gly  Glu  Ala  Glu  Ala  Pro  Ala  Ala  Glu  Gly  Gly
               180                      185                      190

Lys  Asp  Glu  Ala  Ala  Gly  Gly  Ala  Ala  Ala  Ala  Ala  Ala  Glu  Ala  Gly
```

|     |     |     |     | 195 |     |     |     |     | 200 |     |     |     |     | 205 |     |
| --- | --- | --- | --- | --- | --- | --- | --- | --- | --- | --- | --- | --- | --- | --- | --- |
| Ala | Ala | Ser | Gly | Glu | Gln | Ala | Ala | Pro | Gly | Glu | Ala | Ala | Ala |
|     | 210 |     |     |     |     | 215 |     |     |     | 220 |     |     |     |
| Gly | Glu | Glu | Gly | Ala | Ala | Gly | Gly | Asp | Ser | Gln | Glu | Ala | Lys | Pro | Gln |
| 225 |     |     |     |     | 230 |     |     |     |     | 235 |     |     |     |     | 240 |
| Glu | Ala | Ala | Val | Ala | Pro | Glu | Lys | Pro | Pro | Ala | Ser | Asp | Glu | Thr | Lys |
|     |     |     |     | 245 |     |     |     |     | 250 |     |     |     |     | 255 |     |
| Ala | Ala | Glu | Glu | Pro | Ser | Lys | Val | Glu | Lys | Lys | Ala | Glu | Glu | Ala |
|     |     |     | 260 |     |     |     |     | 265 |     |     |     | 270 |     |     |
| Gly | Ala | Ser | Ala | Ala | Ala | Cys | Glu | Ala | Pro | Ser | Ala | Ala | Gly | Leu | Val |
|     |     | 275 |     |     |     |     | 280 |     |     |     |     | 285 |     |     |     |
| Cys | Pro | Arg | Arg | Gly | Gly | Ser | Pro | Arg | Gly | Gly | Ala | Arg | Gly | Arg | Arg |
|     | 290 |     |     |     |     | 295 |     |     |     |     | 300 |     |     |     |     |
| Ser | Leu | Asn | Gln | Ala | Cys | Ala | Ala | Pro | Ser | Gln | Glu | Ala | Gln | Pro | Glu |
| 305 |     |     |     |     | 310 |     |     |     |     | 315 |     |     |     |     | 320 |
| Cys | Ser | Pro | Glu | Ala | Pro | Pro | Ala | Glu | Ala | Glu |
|     |     |     |     | 325 |     |     |     |     | 330 |     |

( 2 ) INFORMATION FOR SEQ ID NO:6:

( i ) SEQUENCE CHARACTERISTICS:
        ( A ) LENGTH: 335 amino acids
        ( B ) TYPE: amino acid
        ( C ) STRANDEDNESS: single
        ( D ) TOPOLOGY: linear ( i i ) MOLECULE TYPE: protein
        ( A ) DESCRIPTION: predicted primary structure of bovine MARCKS ( i i i ) HYPOTHETICAL: NO ( x i ) SEQUENCE DESCRIPTION: SEQ ID NO:6:

| Met | Gly | Ala | Gln | Phe | Ser | Lys | Thr | Ala | Ala | Lys | Gly | Glu | Ala | Thr | Ala |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Glu | Arg | Pro | Gly | Glu | Ala | Ala | Val | Ala | Ser | Ser | Pro | Ser | Lys | Ala | Asn |
|     |     |     | 20 |     |     |     |     | 25 |     |     |     |     | 30 |     |     |
| Gly | Gln | Glu | Asn | Gly | His | Val | Lys | Val | Asn | Gly | Asp | Ala | Ser | Pro | Ala |
|     |     |     | 35 |     |     |     |     | 40 |     |     |     | 45 |     |     |     |
| Ala | Ala | Glu | Pro | Gly | Ala | Lys | Glu | Glu | Leu | Gln | Ala | Asn | Gly | Ser | Ala |
|     |     | 50 |     |     |     |     | 55 |     |     |     |     | 60 |     |     |     |
| Pro | Ala | Ala | Asp | Lys | Glu | Glu | Pro | Ala | Ala | Ala | Gly | Ser | Gly | Ala | Ala |
| 65 |     |     |     |     | 70 |     |     |     |     | 75 |     |     |     |     | 80 |
| Ser | Pro | Ala | Ala | Ala | Glu | Lys | Asp | Glu | Pro | Ala | Ala | Ala | Ala | Pro | Asp |
|     |     |     |     | 85 |     |     |     |     | 90 |     |     |     |     | 95 |     |
| Ala | Gly | Ala | Ser | Pro | Val | Glu | Lys | Glu | Ala | Pro | Val | Glu | Gly | Glu | Ala |
|     |     |     |     | 100 |     |     |     |     | 105 |     |     |     |     | 110 |     |
| Ala | Glu | Pro | Gly | Ser | Pro | Thr | Ala | Ala | Glu | Gly | Glu | Ala | Ala | Ser | Ala |
|     |     |     | 115 |     |     |     |     | 120 |     |     |     |     | 125 |     |     |
| Ala | Ser | Ser | Thr | Ser | Ser | Pro | Lys | Ala | Glu | Asp | Gly | Ala | Thr | Pro | Ser |
|     |     | 130 |     |     |     |     | 135 |     |     |     |     | 140 |     |     |     |
| Pro | Ser | Asn | Glu | Thr | Pro | Lys | Lys | Lys | Lys | Arg | Phe | Ser | Phe | Lys |
| 145 |     |     |     |     | 150 |     |     |     |     | 155 |     |     |     | 160 |
| Lys | Ser | Phe | Lys | Leu | Ser | Gly | Phe | Ser | Phe | Lys | Lys | Asn | Lys | Lys | Glu |
|     |     |     |     | 165 |     |     |     |     | 170 |     |     |     |     | 175 |     |
| Ala | Gly | Glu | Gly | Gly | Glu | Ala | Glu | Gly | Ala | Ala | Gly | Ala | Ser | Ala | Glu |
|     |     |     |     | 180 |     |     |     |     | 185 |     |     |     |     | 190 |     |
| Gly | Gly | Lys | Asp | Glu | Ala | Ser | Gly | Gly | Ala | Ala | Ala | Ala | Ala | Gly | Glu |
|     |     |     | 195 |     |     |     |     | 200 |     |     |     |     | 205 |     |     |

Ala Gly Ala Ala Pro Gly Glu Pro Thr Ala Ala Pro Gly Glu Ala
210                215                     220

Ala Ala Gly Glu Glu Gly Ala Ala Gly Gly Asp Pro Gln Glu Ala Lys
225             230                 235                     240

Pro Glu Glu Ala Ala Val Ala Pro Glu Lys Pro Pro Ala Arg Arg Gly
            245                 250                     255

Ala Lys Ala Val Glu Glu Pro Ser Lys Ala Glu Glu Lys Ala Glu Glu
            260                 265                 270

Ala Gly Val Ser Ala Ala Gly Ala Ala Gly Cys Glu Ala Pro Ser Ala
            275                 280                 285

Ala Gly Pro Gly Cys Pro Arg Ala Gly Gly Ala Pro Arg Glu Glu Ala
            290                 295                 300

Ala Pro Pro Arg Ala Ser Ser Ala Cys Ser Ala Pro Ser Gln Glu Ala
305                 310                 315                 320

Gln Pro Glu Cys Ser Pro Glu Ala Pro Pro Ala Glu Ala Ala Glu
                325                 330                 335

(2) INFORMATION FOR SEQ ID NO:7:

(i) SEQUENCE CHARACTERISTICS:
      (A) LENGTH: 309 amino acids
      (B) TYPE: amino acid
      (C) STRANDEDNESS: single
      (D) TOPOLOGY: linear (ii) MOLECULE TYPE: protein
      (A) DESCRIPTION: predicted primary structure of murine MARCKS (iii) HYPOTHETICAL: NO (xi) SEQUENCE DESCRIPTION: SEQ ID NO:7:

Met Gly Ala Gln Phe Ser Lys Thr Ala Ala Lys Gly Glu Ala Thr Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala
            35                  40                  45

Ala Ala Glu Pro Gly Ala Lys Glu Glu Leu Gln Ala Asn Gly Ser Ala
    50                  55                  60

Pro Ala Ala Asp Lys Glu Glu Pro Ala Ser Gly Ser Ala Ala Thr Pro
65                  70                  75                  80

Ala Ala Ala Glu Lys Asp Glu Ala Ala Ala Ala Thr Glu Pro Gly Ala
                85                  90                  95

Gly Ala Ala Asp Lys Glu Ala Ala Glu Ala Glu Pro Ala Glu Pro Ser
            100                 105                 110

Ser Pro Ala Ala Glu Ala Glu Gly Ala Ser Ala Ser Ser Thr Ser Ser
        115                 120                 125

Pro Lys Ala Glu Asp Gly Ala Ala Pro Ser Pro Ser Ser Glu Thr Pro
    130                 135                 140

Lys Lys Lys Lys Lys Arg Phe Ser Phe Lys Lys Ser Phe Lys Leu Ser
145                 150                 155                 160

Gly Phe Ser Phe Lys Lys Ser Lys Lys Glu Ser Gly Glu Gly Ala Glu
                165                 170                 175

Ala Glu Gly Ala Thr Ala Glu Gly Ala Lys Asp Glu Ala Ala Ala Ala
            180                 185                 190

Ala Gly Gly Glu Gly Ala Ala Ala Pro Gly Glu Gln Ala Gly Gly Ala
        195                 200                 205

```
Gly  Ala  Glu  Gly  Ala  Ala  Gly  Gly  Glu  Pro  Arg  Glu  Ala  Glu  Ala  Ala
     210                           215                      220

Glu  Pro  Glu  Gln  Pro  Glu  Gln  Pro  Glu  Gln  Pro  Ala  Ala  Glu  Glu  Pro
225                      230                      235                           240

Gln  Ala  Glu  Glu  Gln  Ser  Glu  Ala  Ala  Gly  Glu  Lys  Ala  Glu  Glu  Pro
               245                           250                           255

Ala  Pro  Gly  Ala  Thr  Ala  Gly  Asp  Ala  Ser  Ser  Ala  Ala  Gly  Pro  Glu
               260                      265                      270

Gln  Glu  Ala  Pro  Ala  Ala  Thr  Asp  Glu  Ala  Ala  Ala  Ser  Ala  Ala  Pro
          275                      280                      285

Ala  Ala  Ser  Pro  Glu  Pro  Gln  Pro  Glu  Cys  Ser  Pro  Glu  Ala  Pro  Pro
     290                      295                      300

Ala  Pro  Thr  Ala  Glu
305
```

( 2 ) INFORMATION FOR SEQ ID NO:8:

( i ) SEQUENCE CHARACTERISTICS:
        ( A ) LENGTH: 309 amino acids
        ( B ) TYPE: amino acid
        ( C ) STRANDEDNESS: single
        ( D ) TOPOLOGY: linear ( i i ) MOLECULE TYPE: protein
        ( A ) DESCRIPTION: predicted primary structure of rat MARCKS ( i i i ) HYPOTHETICAL: NO ( x i ) SEQUENCE DESCRIPTION: SEQ ID NO:8:

```
Met  Gly  Ala  Gln  Phe  Ser  Lys  Thr  Ala  Ala  Lys  Gly  Glu  Ala  Ala  Ala
1                        5                        10                       15

Glu  Arg  Pro  Gly  Glu  Ala  Ala  Val  Ala  Ser  Ser  Pro  Ser  Lys  Ala  Asn
               20                       25                       30

Gly  Gln  Glu  Asn  Gly  His  Val  Lys  Val  Asn  Gly  Asp  Ala  Ser  Pro  Ala
               35                       40                       45

Ala  Ala  Glu  Pro  Gly  Ala  Lys  Glu  Glu  Leu  Gln  Ala  Asn  Gly  Ser  Ala
     50                       55                       60

Pro  Ala  Ala  Asp  Lys  Glu  Glu  Pro  Ala  Ser  Gly  Gly  Ala  Ala  Thr  Pro
65                       70                       75                            80

Ala  Ala  Ala  Asp  Lys  Asp  Glu  Ala  Ala  Ala  Pro  Glu  Pro  Gly  Ala
                    85                       90                       95

Ala  Thr  Ala  Asp  Lys  Glu  Ala  Ala  Glu  Ala  Glu  Pro  Ala  Glu  Pro  Gly
               100                      105                      110

Ser  Pro  Ser  Ala  Glu  Thr  Glu  Gly  Ala  Ser  Ala  Ser  Ser  Thr  Ser  Ser
          115                      120                      125

Pro  Lys  Ala  Glu  Asp  Gly  Ala  Ala  Pro  Ser  Pro  Ser  Ser  Glu  Thr  Pro
130                      135                      140

Lys  Lys  Lys  Lys  Lys  Arg  Phe  Ser  Phe  Lys  Lys  Ser  Phe  Lys  Leu  Ser
145                      150                      155                           160

Gly  Phe  Ser  Phe  Lys  Lys  Ser  Lys  Lys  Glu  Ala  Gly  Glu  Gly  Ala  Glu
                    165                      170                      175

Ala  Glu  Gly  Ala  Thr  Ala  Asp  Gly  Ala  Lys  Asp  Glu  Ala  Ala  Ala  Ala
               180                      185                      190

Ala  Gly  Gly  Asp  Ala  Ala  Ala  Ala  Pro  Gly  Glu  Gln  Ala  Gly  Gly  Ala
          195                      200                      205

Gly  Ala  Glu  Gly  Ala  Glu  Gly  Gly  Glu  Ser  Arg  Glu  Ala  Glu  Ala  Ala
     210                      215                      220

Glu  Pro  Glu  Gln  Pro  Glu  Gln  Pro  Glu  Gln  Pro  Ala  Ala  Glu  Glu  Pro
```

```
            225                 230                     235                     240
Arg  Ala  Glu  Glu  Pro  Ser  Glu  Ala  Val  Gly  Glu  Lys  Ala  Glu  Glu  Pro
                    245                      250                          255

Ala  Pro  Gly  Ala  Thr  Ala  Asp  Asp  Ala  Pro  Ser  Ala  Ala  Gly  Pro  Glu
               260                 265                           270

Gln  Glu  Ala  Pro  Ala  Ala  Thr  Asp  Glu  Pro  Ala  Ala  Ser  Ala  Ala  Ser
          275                      280                      285

Ala  Ala  Ser  Pro  Glu  Pro  Gln  Pro  Glu  Cys  Ser  Pro  Glu  Ala  Pro  Pro
          290                 295                      300

Ala  Pro  Val  Ala  Glu
305
```

( 2 ) INFORMATION FOR SEQ ID NO:9:

( i ) SEQUENCE CHARACTERISTICS:
        ( A ) LENGTH: 281 amino acids
        ( B ) TYPE: amino acid
        ( C ) STRANDEDNESS: single
        ( D ) TOPOLOGY: linear ( i i ) MOLECULE TYPE: protein
        ( A ) DESCRIPTION: predicted primary structure of chicken MARCKS ( i i i ) HYPOTHETICAL: NO ( x i ) SEQUENCE DESCRIPTION: SEQ ID NO:9:

```
Met  Gly  Ala  Gln  Phe  Ser  Lys  Thr  Ala  Ala  Lys  Gly  Glu  Ala  Ala  Ala
1                   5                        10                          15

Glu  Lys  Pro  Gly  Glu  Ala  Val  Ala  Ala  Ser  Pro  Ser  Lys  Ala  Asn  Gly
               20                      25                      30

Gln  Glu  Asn  Gly  His  Val  Lys  Val  Asn  Gly  Asp  Ala  Ser  Pro  Ala  Ala
          35                      40                      45

Ala  Glu  Ala  Gly  Lys  Glu  Glu  Val  Gln  Ala  Asn  Gly  Ser  Ala  Pro  Ala
     50                       55                      60

Glu  Glu  Thr  Gly  Lys  Glu  Glu  Ala  Ala  Ser  Ser  Glu  Pro  Ala  Ser  Glu
65                       70                      75                        80

Lys  Glu  Ala  Ala  Glu  Ala  Glu  Ser  Thr  Glu  Pro  Ala  Ser  Pro  Ala  Trp
                    85                      90                           95

Gly  Glu  Ala  Ser  Pro  Lys  Thr  Glu  Glu  Gly  Ala  Thr  Pro  Ser  Ser  Ser
               100                     105                     110

Ser  Glu  Thr  Pro  Lys  Lys  Lys  Lys  Lys  Arg  Phe  Ser  Phe  Lys  Lys  Ser
               115                     120                     125

Phe  Lys  Leu  Ser  Gly  Phe  Ser  Phe  Lys  Lys  Asn  Lys  Lys  Glu  Ala  Gly
     130                     135                     140

Glu  Gly  Ala  Glu  Ser  Glu  Gly  Gly  Ala  Ala  Ala  Ala  Glu  Gly  Gly  Gly
145                     150                     155                       160

Lys  Glu  Glu  Ala  Ala  Ala  Ala  Ala  Pro  Glu  Ala  Ala  Gly  Gly  Glu  Glu
                    165                     170                          175

Gly  Lys  Ala  Ala  Ala  Glu  Glu  Ala  Ser  Ala  Ala  Ala  Ala  Gly  Ser  Arg
                    180                     185                          190

Glu  Ala  Ala  Lys  Glu  Glu  Ala  Gly  Asp  Ser  Gln  Glu  Ala  Lys  Ser  Asp
               195                     200                     205

Glu  Ala  Ala  Pro  Glu  Asp  Ala  Thr  Gly  Glu  Glu  Ala  Pro  Ala  Ala  Glu
          210                     215                     220

Glu  Gln  Gln  Gln  Gln  Gln  Gln  Gln  Glu  Lys  Ala  Ala  Glu  Glu  Ala  Gly
225                     230                     235                       240

Ala  Ala  Ala  Thr  Ser  Glu  Ala  Gly  Ser  Gly  Glu  Gln  Glu  Ala  Ala  Pro
                    245                     250                          255
```

|     |     |     |     |     |     |     |     |     |     |     |     |     |     |     |
| --- | --- | --- | --- | --- | --- | --- | --- | --- | --- | --- | --- | --- | --- | --- |
| Ala | Glu | Glu | Pro | Ala | Ala | Ala | Arg | Gln | Glu | Ala | Pro | Ser | Glu | Ser | Ser |
|     |     |     | 260 |     |     |     |     | 265 |     |     |     | 270 |     |     |
| Pro | Glu | Gly | Pro | Ala | Glu | Pro | Ala | Glu |
|     |     | 275 |     |     |     | 280 |

(2) INFORMATION FOR SEQ ID NO:10:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ii) MOLECULE TYPE: cDNA
        (A) DESCRIPTION: rabbit alveolar macrophage MacMARCKS (iii) HYPOTHETICAL: NO (iv) ANTI-SENSE: NO (ix) FEATURE:
        (A) NAME/KEY: CDS
        (B) LOCATION: 196..793

(xi) SEQUENCE DESCRIPTION: SEQ ID NO:10:

```
GCTTTAGAGA  GCGGCAGCGG  CGGGCGGCGT  AGCTAGCGGG  TCGGCCCGGA  GCGGGGGTGC      60

AGCTCGGTTT  CCCCCGACAC  CCCCTCCCCC  TCAGGCGCTC  AGCCCCACCC  CTCTGCGGGC     120

CGGGCCGACC  CCACCGAACT  ATCCCCTGCG  GCGCGAGCCC  GGCGCTCCGG  GCGCCCCCAA     180

CAGACCCCCC  CCACC ATG GGC AGC CAG AGC TCC AAG GCT CCC CGG GGC GAC         231
                Met Gly Ser Gln Ser Ser Lys Ala Pro Arg Gly Asp
                 1               5                        10
```

| GTG | ACC | GCC | GAG | GAG | GCA | GCA | GGC | GCT | TCC | CCC | GCG | AAG | GCC | AAC | GGA | 279 |
| --- | --- | --- | --- | --- | --- | --- | --- | --- | --- | --- | --- | --- | --- | --- | --- | --- |
| Val | Thr | Ala | Glu | Glu | Ala | Ala | Gly | Ala | Ser | Pro | Ala | Lys | Ala | Asn | Gly |
|     |     |     | 15  |     |     |     |     | 20  |     |     |     |     | 25  |

| CAG | GAG | AAT | GGC | CAC | GTG | AAA | AGC | AAT | GGA | GAC | TTA | ACC | CCC | AAG | GGT | 327 |
| --- | --- | --- | --- | --- | --- | --- | --- | --- | --- | --- | --- | --- | --- | --- | --- | --- |
| Gln | Glu | Asn | Gly | His | Val | Lys | Ser | Asn | Gly | Asp | Leu | Thr | Pro | Lys | Gly |
|     | 30  |     |     |     |     | 35  |     |     |     |     | 40  |

| GAA | GGG | GAG | TCG | CCC | CCC | GTG | AAC | GGA | ACA | GAT | GAG | GCA | GCT | GGG | GCC | 375 |
| --- | --- | --- | --- | --- | --- | --- | --- | --- | --- | --- | --- | --- | --- | --- | --- | --- |
| Glu | Gly | Glu | Ser | Pro | Pro | Val | Asn | Gly | Thr | Asp | Glu | Ala | Ala | Gly | Ala |
| 45  |     |     |     | 50  |     |     |     |     | 55  |     |     |     |     |     | 60  |

| ACT | GGC | GAT | GCG | ATC | GAG | CCA | GCA | CCC | CCT | AGC | CAG | GGC | GCC | GAG | GCC | 423 |
| --- | --- | --- | --- | --- | --- | --- | --- | --- | --- | --- | --- | --- | --- | --- | --- | --- |
| Thr | Gly | Asp | Ala | Ile | Glu | Pro | Ala | Pro | Pro | Ser | Gln | Gly | Ala | Glu | Ala |
|     |     |     |     | 65  |     |     |     |     | 70  |     |     |     |     | 75  |

| AAG | GGG | GAC | GCC | CCC | CCC | AAG | GAG | ACC | CCC | AAT | GCG | AAG | AAG | AAG | AAA | 471 |
| --- | --- | --- | --- | --- | --- | --- | --- | --- | --- | --- | --- | --- | --- | --- | --- | --- |
| Lys | Gly | Asp | Ala | Pro | Pro | Lys | Glu | Thr | Pro | Asn | Ala | Lys | Lys | Lys | Lys |
|     |     |     |     | 80  |     |     |     |     | 85  |     |     |     |     | 90  |

| TTC | TCT | TTC | AAG | CCT | TTC | AAA | TTG | AGC | GGC | CTG | TCC | TTC | AAG | AGA | AAT | 519 |
| --- | --- | --- | --- | --- | --- | --- | --- | --- | --- | --- | --- | --- | --- | --- | --- | --- |
| Phe | Ser | Phe | Lys | Pro | Phe | Lys | Leu | Ser | Gly | Leu | Ser | Phe | Lys | Arg | Asn |
|     |     |     |     | 95  |     |     |     |     | 100 |     |     |     |     | 105 |

| CGG | AAG | GAG | GGC | GGG | GGC | GAC | TCC | TCT | GCC | TCC | TCC | CCC | ACG | GAG | GAA | 567 |
| --- | --- | --- | --- | --- | --- | --- | --- | --- | --- | --- | --- | --- | --- | --- | --- | --- |
| Arg | Lys | Glu | Gly | Gly | Gly | Asp | Ser | Ser | Ala | Ser | Ser | Pro | Thr | Glu | Glu |
|     | 110 |     |     |     |     | 115 |     |     |     |     | 120 |

| GAG | CAG | GAG | CAG | GGC | GAG | ATC | GGT | GCC | TGC | AGC | GAA | GAG | GGC | ACT | GCC | 615 |
| --- | --- | --- | --- | --- | --- | --- | --- | --- | --- | --- | --- | --- | --- | --- | --- | --- |
| Glu | Gln | Glu | Gln | Gly | Glu | Ile | Gly | Ala | Cys | Ser | Glu | Glu | Gly | Thr | Ala |
| 125 |     |     |     |     | 130 |     |     |     |     | 135 |     |     |     |     | 140 |

| CCG | GAG | GGG | AAG | GCC | GCT | GCC | ACC | CCG | GAG | AGC | CAG | GAG | CCC | CAG | GCC | 663 |
| --- | --- | --- | --- | --- | --- | --- | --- | --- | --- | --- | --- | --- | --- | --- | --- | --- |
| Pro | Glu | Gly | Lys | Ala | Ala | Ala | Thr | Pro | Glu | Ser | Gln | Glu | Pro | Gln | Ala |
|     |     |     |     | 145 |     |     |     |     | 150 |     |     |     |     | 155 |

| AAG | GGG | GCA | GAG | GCT | GGC | GCT | GCC | TGC | AAG | GGA | GGA | GAC | ACA | GAA | GAG | 711 |
| --- | --- | --- | --- | --- | --- | --- | --- | --- | --- | --- | --- | --- | --- | --- | --- | --- |
| Lys | Gly | Ala | Glu | Ala | Gly | Ala | Ala | Cys | Lys | Gly | Gly | Asp | Thr | Glu | Glu |
|     |     |     |     | 160 |     |     |     |     | 165 |     |     |     |     | 170 |

| GAG | GCA | GGG | CCC | CCA | GCA | GAG | CCG | TCC | ACT | CCC | TCG | GGG | CCG | GAG | AGT | 759 |

-continued

Glu Ala Gly Pro Pro Ala Glu Pro Ser Thr Pro Ser Gly Pro Glu Ser
        175                 180                 185

GGC CCT ACA CCG GCC GGC GCC GAG CAG AAT GAG T AGCTGGGTGG              803
Gly Pro Thr Pro Ala Gly Ala Glu Gln Asn Glu
    190                 195

GGGCAGGCGG GTGATCTCTT AAGCTACAAA AAACTGTGCT GTCCTTGTGA GGTCACTGCC     863

TGGACCCTGT GCCCTGGCTG CCTTCCTGTG CCCAGAAAGG AGGGGCTGCT GCGCTCCAAC     923

CACTTCCCTC TCCTCCTCTC CCTCCTGTGG ATTCTCCCAT CAGCCATCTG GTCTTCCTCG     983

CAAGGCCAGC TGAAGATGGT CCCTTACATT TTCCCAAGTT AGGTTAGTGA TGTGAAATGC    1043

TCCTGGTCCA GCCCCCTCCC CTGACCCCCC CACCCCTGCC CTGCAGAAGG CAATTGCTGG    1103

TTTTCTCCCT CGGTTCTTTT CCAAGTAGGT TCTGTTTACC CTACTCCCCC AAATCCCTGA    1163

GCCAGAAGTG GGGTGCTTAT CCCCCAAACC CTGAGTGTCC AGCCTTCCCC TGTTGAGTTT    1223

TTAGTCTCTT GTGCTGTGCC TAGTGGCACC TGGGCTGGGG AGGACACTGC CCCTGTCTGG    1283

GTTTTTATAA ATGTCTTACT CAAGTTCAAA CCTCCAGCTT GTGAATCAAC TGGTGTCTCT    1343

TTTTTGACTT GGTAAGCAAG TATTAGGCTT TGGGGTGGGG GAAGTCTGTA ATGTGAAACA    1403

ACTTCTTGTT GTCTTTTTCT CCCATTGTTG TAAATAACTT TTAATGGCCA AACCCCAGAT    1463

TTGTACTTTT TTTTTCTAAT TGCTAAAACC ATTCTCTTCC ACCTGGTTTT ACTGTAACCT    1523

TTGGAAAAGG AATAAATGTT GTCCCTTTAA AAAAAAAAA AAA                       1566

( 2 ) INFORMATION FOR SEQ ID NO:11:

( i ) SEQUENCE CHARACTERISTICS:
          ( A ) LENGTH: 18 amino acids
          ( B ) TYPE: amino acid
          ( C ) STRANDEDNESS: single
          ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:11:

Lys Lys Phe Ser Phe Lys Lys Pro Phe Lys Leu Ser Gly Leu Ser Phe
    1               5                   10                  15

Lys Arg ( 2 ) INFORMATION FOR SEQ ID NO:12:

( i ) SEQUENCE CHARACTERISTICS:
          ( A ) LENGTH: 18 amino acids
          ( B ) TYPE: amino acid
          ( C ) STRANDEDNESS: single
          ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:12:

Lys Arg Phe Ser Phe Lys Lys Ser Phe Lys Leu Ser Gly Phe Ser Phe
    1               5                   10                  15

Lys Lys

METHOD FOR THE DETECTION OF ANENCEPHALY

GOVERNMENTAL SUPPORT

This invention was made with governmental support under NIH A132972. The U.S. government has certain rights in the invention.

BACKGROUND OF THE INVENTION

1. Field of the Invention

This invention relates to a method for detection of anencephaly using a nucleic acid coding for a protein kinase C substrate. In particular, the protein kinase C substrate is a member of the MARCKS family of protein kinases.

2. Description of the Related Art

When macrophages encounter Gram negative bacteria a number of protein kinase C (PKC)-dependent signal-transduction pathways are activated. These lead to the cytoskeletal rearrangements necessary for phagocytosis and migration, the release of inflammatory mediators such as prostaglandins and leukotrienes, and the secretion of hydrolytic enzymes and reactive oxygen intermediates. Bacterial lipopolysaccharide (LPS) or endotoxin, the major surface component of gram-negative bacteria, has a profound modulatory effect on PKC-dependent responses. LPS alone does not activate PKC, but it primes macrophages for vastly potentiated responses when the cells subsequently encounter PKC-activating agonists. Concomitant with priming, LPS induces the synthesis of two myristoylated proteins with apparent molecular masses of 68K and 42K, respectively.

LPS or endotoxin, a major surface component of Gram negative bacteria is a potent activator of cellular and humoral immunity. LPS enhances the tumoricidal activity of macrophages and stimulates the release of numerous inflammatory mediators such as tumor necrosis factor, arachidonic acid metabolites, complement components, reactive oxygen intermediates, nitric oxide, and hydrolytic enzymes.

Much has been learned recently about the mechanism by which cells recognize LPS. LPS associates with LPS binding protein, and the resulting complex promotes the binding of LPS to CD14 on the cell surface. CD14 appears to be a subunit of a multicomponent LPS receptor. A 70 kDa membrane protein, the scavenger receptor, and the CD11b/CD18 complex have all been demonstrated to bind LPS, but the significance of this is not known. A recent report has cast doubt on the identity of the 70 kDa protein as an LPS receptor. Binding of LPS to CD14 causes rapid protein tyrosine phosplhorylation of a number of intracellular proteins that include three members or the MAP kinase family (MAPK1, MAPK4 and p38). p38 is homologous to the *S. cerevisiae* HOG1 gene product, which is involved in osmotic regulation. Data from a number of laboratories indicate that protein kinase C (PKC) induced phosplhorylation is necessary for a full functional response to LPS. LPS primes macrophages for enhanced PKC mediated responses, and promotes the synthesis of two PKC substrates, MARCKS and MacMARCKS. Because LPS treatment also potentiates the phosplhorylation of these proteins, they are ideal candidates as effectors of LPS-induced responses.

LPS induces profound changes in gene expression in macrophages, often by activation of the NFκB transcription factor. Recent investigations into the promoter region of the i-NOS gene have demonstrated two regions which are required for LPS-dependent transcription, and both of these regions contain NFκB binding sites. However, the NFκB binding sites were found by computer analysis of the region, and the participation of NFκB in transcriptional activation of i-NOS was not confirmed by site directed mutagenesis. Investigation into the 5' upstream sequence of another LPS responsive gene, Rantes, demonstrated the importance of an NFκB binding site, as well as the 3' half of the proximal AP1 site. It is therefore clear that a great deal of complexity exists in the transcriptional activation of LPS responsive genes.

The 68K protein induced by LPS, myristoylated alanine-rich protein kinase C substrate (MARCKS), is a major cellular substrate of PKC that binds calmodulin and has a role in diverse cellular processes including macrophage and neutrophil activation, mitogenesis, and neurosecretion, and may regulate the reversible attachment of the actin cytoskeleton with the substrate-adhlerent plasma membrane in motile phagocytes. (Li et al (1992) *Cell* 70:791–801).

PKC phosphorylation produces translocation of MARCKS from membrane to cytoplasm in many cells. The binding of MARCKS to biological membranes appears to require both hydrophobic insertion of its myristoyl chain into the lipid bilayer and electrostatic interaction of its basic domain with acidic lipids (Kim et al (1994) *J. Biol. Chem.* 269:28214–28219). The amino-terminal glycine of MARCKS is myristoylated, and the protein is rich in acidic residues except for one basic region. The murine protein for example contains a cluster of 13 basic and 0 acidic residues between amino acids 145 and 169. This basic region is highly conserved, contains the only serines phosphorylated by PKC, binds calmodulin (CaM) in a calcium-dependent manner, and binds actin filaments (Kim et al, 1994).

In addition to hydrophobic and electrostatic interactions with phospholipid bilayers, there is good experimental evidence that the binding of MARCKS to biological membranes also involves specific protein-protein interactions. The punctate distribution of MARCKS in macrophage membranes suggests the protein also interacts with cytoskeletal elements. These protein-protein interactions need not be strong because once MARCKS is bound to the bilayer component of the membrane via its myristoyl chain and basic domain, even a weak protein-protein interaction would suffice to create a punctate distribution. Weak protein-protein interactions may also target MARCKS to specific membranes (e.g., the plasma rather than Golgi membranes) (Kim et al, 1994).

The cDNA encoding MARCKS has been cloned and sequenced from a number of species. The actual molecular mass of MARCKS, calculated from its primary structure, ranges from 28 kd to 31 kd, while its apparent molecular mass determined by SDS-PAGE varies from 67K to 87K. This anomalous migration on SDS gels can be ascribed to the high axial ratio and rod-shaped dimensions of MARCKS. Comparison of the sequences reveals that MARCKS contains two highly conserved domains: an N-terminal domain that contains the myristoylation site and which appears to function in membrane binding, and an effector domain, located in the middle of the rod-shaped protein, that contains all the serine residues known to be phosphorylated, as well as the calmodulin and actin binding sites. The proximity of the phosphorylation sites to the actin and calmodulin binding sites explains the reciprocal regulation of phosphorylation and the binding of these two proteins (Li et al, 1992).

The 42K myristoylated protein induced during LPS priming is a PKC substrate that shares the effector domain of MARCKS, but has a distinct N-terminal membrane-binding domain. Like MARCKS, this 42K protein is an alanine-rich protein that binds calmodulin in a manner regulated by PKC. Since the 42K protein is structurally and functionally related to MARCKS and since it is predominantly expressed in LPS-stimulated macrophages, it has been named Mac-MARCKS.

MacMARCKS, like MARCKS, is heat stable. Mac-MARCKS has been cloned from an LPS-induced rabbit alveolar macrophage cDNA library. The transfected rabbit cDNA encodes a myristoylated protein that migrates on 2D IEF-SDS-PAGE with an apparent molecular mass of 42K and a pI of 4.2, as does the in vitro translated protein (Li et al, 1992).

The rabbit MacMARCKS protein sequence shares a 92% identity with the murine protein sequence. Moreover, a comparison of rabbit and murine MacMARCKS with human, bovine, murine, rat and chicken MARCKS reveals a similar domain structure. Both have myristoylated N-termini that differ in amino acid sequence but contain similar charge distributions: two positive charges followed by two negative charges. The myristoylation domain is followed by two regions of major homology (MH1 and MH2). However, there is an important difference between MARCKS and MacMARCKS: the sequence FKKS (SEQ ID NO:1) that comprises the second of 2 phosphopeptides of MARCKS is FKKP (SEQ ID NO:2) of MacMARCKS, accounting for the absence of a phosphopeptide 2 in phosphorylated MacMARCKS.

Several lines of evidence suggest that MARCKS and MacMARCKS are members of a protein family. Both are acidic, myristoylated PKC substrates with similar and unusual amino acid compositions: alanine, glycine, proline and glutamic acid comprise approximately 60% of the total amino acids of both proteins. Both proteins have a similar domain structure: an N-terminal myristoylated domain, a highly conserved MH2 domain, and a basic effector domain that contains the phosphorylation sites and the calmodulin binding site.

Both MacMARCKS and MARCKS contain the myristic acid moiety in an amide linkage to an N-terminal glycine residue. Myristoylation is absolutely required for membrane binding of a number of important signal-transducing molecules including MARCKS, certain a subunits of the heterotrimeric G-proteins, and the src family of tyrosine kinases. Evidence suggests that myristoylated proteins do not associate with membranes by the mere insertion of the fatty acid moiety into the lipid bilayer; rather, they associate with specific receptors at the inner leaf of the plasma membrane. The specific association of MARCKS with focal contacts also suggests a receptor at the cytoplasmic face of the substrate-adherent plasma membrane. Mutational analysis suggests that the first 14 amino acids of MARCKS are essential for appropriate targeting, but since MacMARCKS and MARCKS differ in their first 20 amino acids, it its likely that they are targeted to different subcellular locations. However, given the similarity between the effector domains of MARCKS and MacMARCKS, it is likely that Mac-MARCKS also binds actin (Li et al, 1992).

MARCKS is widely distributed and has been implicated in cell motility, secretion, the regulation of the cell cycle, and transformation. MARCKS binds Ca calmodulin and F-actin, and this is regulated by phosphorylatlon. MARCKS cycles between the membrane and cytosol, and has been proposed to serve as a regulator of actin structure at the membrane, and of actin-membrane interactions. In contrast to MARCKS, MacMARCKS has a restricted distribution, and is mainly found in cells which have a high capacity for directed membrane traffic such as macrophages, neurons, and epithelial cells. Although MARCKs and MacMARCKs have a similar domain structure, and bind calmodulin and actin, they clearly have distinct functions. While MARCKS associates with the apical surface of polarized epithelial cells, MacMARCKS is targeted to the basolateral surface. MARCKS cycles reversibly between the membrane and the cytosol, while MacMARCKS always remains associated with the membrane. MARCKS has a role in actin remodeling in motility and phagocytosis, while MacMARCKS is apparently associated with vesicular traffic, and the recruitment of membranes to phagosomes. Interestingly, unlike MARCKS, MacMARCKS is not expressed in neutrophils, consistent with the thesis that these proteins serve different functions during phagocytosis.

Phagocytosis is an ancient adaptation which allows lower organisms to ingest nutrients, and higher organisms to capture and sterilize pathogens, to remove senescent material, and remodel tissues. Macrophages, monocytes, and neutrophils are considered "professional" phagocytes because of their dedication to this task. After internalization, phagosomes mature, ultimately fusing with lysosomes. Actin is required for phagocytosis, and perhaps has a role in regulating phagosome-lysosome fusion by temporally controlling access of lysosomes to the phagosomal membrane. However, the signal transduction pathways which regulate phagocytosis, and particularly phagosome-lysosome fusion, are obscure. $Ca^{2+}$ has been implicated as a regulator of phagosome-lysosome fusion, and activated PKC has been shown to associate with the phagosome. Since Mac-MARCKS associates with phagosomes just before phagosome-lysosome fusion, and since its activity is regulated by $Ca^{2+}$/calmodulin and PKC, it is a good candidate molecule to integrate $Ca^{2+}$ and PKC dependent signals in controlling phagosome-lysosome fusion.

Many microorganisms evade killing by circumventing specific steps in the phagocytic pathway. For example, *Salmonella typhimurium* enters macrophages via a spacious phagosoine which resembles a macropinosome. Although this structure subsequently fuses with lysosomes, its acidification is attenuated. In contrast, the IgG opsonized bacterium, and certain PhoP mutants of *S. typhimuriuin*, enter macrophages in phagosomes in which the membrane is tightly apposed to the particle. MacMARCKS associates with tight phagosomes containing dead *S. typhimurium*, or avirulent *S. minnesota*, but not with spacious phagosomes containing the virulent *S. typhimurium*. The relationship between MacMARCKS, virulence, and phagosome morphology will be investigated.

Transcytosis in polarized epithelial cells: Polarized epithelial cells play key roles in immune defense in addition to their barrier function; they both deliver antigens to the mucosal immune system, and export immunoglobulins into secretions that bathe the epithelial surfaces of mucosal tissues. Thus transcytosis across polarized epithelial cells constitutes a major limb of host response to infection. The best characterized examples of transcytosis involve the transport of immunoglobulins (Ig) across epithelia by the polymeric Ig receptor. The newly synthesized receptor is sorted to the basolateral surface, where it binds Pig, is endocytosed, transcytosed, and exocytosed at the apical surface. Little is known about the signaling systems which regulate transcytosis of the pIgR, although PKC and $Ca^{2+}$/calmodulin have been implicated. MacMARCKS is a PKC substrate which binds $Ca^{2+}$/calmodulin and which translocates from the basolateral to the apical surface of epithelial cells when phosphorylated. It therefore represents an excellent candidate as a regulator of transcytosis in epithelial cells.

MARCKS and MacMARCKS bear strong functional similarity to a neurospecific PKC substrate known as GAP-43 or neuromodulin (Liu et al (1990) *Trends Pharmacol. Sci.* 11:107–111). In contrast to MARCKS and MacMARCKS, which bind calmodulin in a calcium-dependent manner, GAP-43 associates with calmodulin in the absence of calcium. Moreover, unlike MARCKS and MacMARCKS, which are myristoylated at their N-termini, GAP-43 is palmitoylated. Both MARCKS and GAP-43 appear to have a role in regulating the motile cytoskeleton. GAP-43 associates with the actin cytoskeleton in neuronal growth cones and is a member of a family of proteins which includes neurogranin, a smaller protein which also contains a phosphorylation domain and calmodulin-binding site.

Another related PKC substrate is adducin, a protein which promotes the association of actin with spectrin in a calmodulin-regulated manner. Adducin has both structural and functional similarities to MARCKS and MacMARCKS (Joshi et al (1991) *J. Cell Biol.* 115:665–675). The protein is composed of highly homologous α and β subunits; both subunits contain identical stretches of 22 amino acids in their C-termini with sequence similarity to the effector domains of MARCKS and MacMARCKS (Joshi et al, 1991). The C-termini of the α and β subunits of adducin also bear the PKC phosplhorylation sites and the domain that binds calcium-calmodulin (Joshi et al, 1991).

Moreover, the following observations indicate that MacMARCKS and members of the MARCKS family of PKC substrates have a role in regulating cell movement and membrane traffic: (1) the effector domain regulates actin crosslinking and calcium-calmodulin binding; (2) the myristoylation domain mediates membrane binding; and (3) the MH2 domain has a role in subcellular targeting.

Little is known about the signal transduction pathways involved in mediating neural tube formation and closure, but studies with drugs implicate both the microtubules and microfilaments. It would thus be advantageous to analyze the role of MacMARCKS in such regulatory processes.

SUMMARY OF THE INVENTION

Accordingly, a major object of the present invention is to provide a method of detecting anencephaly including the steps of:
(a) hybridizing a detectably labelled nucleic acid probe specific for a gene encoding a protein having the following characteristics:
  (i) being a protein kinase C substrate: and
  (ii) binding to calcium-calmodulin; to a cell of fetal, chorionic or amniotic origin under conditions suitable for binding of the probe to the gene;
(b) detecting the presence or absence of binding; and
(c) correlating the absence of binding to a genetic defect leading to anencephaly.

Another object of the invention is to provide an anencephalic mouse embryo null for the gene which is a protein kinase C substrate and binds to calcium-calmodulin.

Another object of the invention is to provide an epithelial cell isolated from the aforesaid anencephalic mouse embryo.

Yet another object of the invention is to provide a hematopoietic cell isolated from the aforesaid anencephalic mouse embryo.

Still another object of the invention is to provide a macrophage isolated from the aforesaid anencephalic mouse embryo.

A further object of the invention is to provide a kit for the detection of anencephaly which includes:

(a) the detectably labelled probe for the protein kinase C substrate; and
(b) a cell null for the gene which is a protein kinase C substrate and binds calcium-calmodulin, to be used as a negative control.

Briefly, the present invention features a method for detecting anencephaly using a probe to a gene encoding a protein kinase C substrate which binds calcium-calmodulin, and which is also involved in actin association and/or regulating cell movement and/or membrane trafficking. Preferably, the gene is a member of the MARCKS family of protein kinase C substrates, and more preferably, it is the MacMARCKS gene.

The invention also features mouse embryos which are null for that gene, which can be used as sources for MacMARCKS null cells. Such cells include epithelial cells and hematopoietic cells, and particularly macrophages. These cells can be used for reconstituting irradiated organisms, to provide an in vivo system for analysis of molecular mechanisms of MacMARCKS, and as model systems for testing the efficacy of drugs and other therapies, including gene therapy. Such drugs and therapies would be directed to reconstituting MacMARCKS-related activities, such as membrane trafficking and regulating cell movement.

Also featured in the present invention are kits including a probe to a gene encoding a protein kinase C substrate having calcium-calmodulin binding activity and MacMARCKS-related activities, and a cell which is null for that gene for use as a negative control.

With the foregoing and other objects, advantages and features of the invention that will become hereinafter apparent, the nature of the invention may be more clearly understood by reference to the following detailed description of the preferred embodiments of the invention and to the appended claims, taken in conjunction with the following illustrative drawings.

BRIEF DESCRIPTION OF THE DRAWINGS

FIG. 1A–1C shows the sequence of rabbit and murine MacMARCKS proteins. FIG. 1A and 1B show the cDNA SEQ ID NO:10 and the predicted amino acid sequence for rabbit alveolar macrophage MacMARCKS (SEQ ID NO:3). The N-terminal myristoylation consensus sequence is shown in bold letters, and the phosphorylation domain is denoted by bold italic letters. The protein sequence obtained from tryptic peptides derived from purified MacMARCKS is underlined. FIG. 1C is a comparison of rabbit alveolar macrophage MacMARCKS (SEQ ID NO:3) and murine resident peritoneal macrophage MacMARCKS (SEQ ID NO:4).

FIG. 2 is a comparison of the primary structure of MacMARCKS and MARCKS. FIG. 2A is a comparison of the predicted primary structure of human (SEQ ID NO:5) (Harlan et al (1991) *J. Biol. Chem.* 266:14399–14405), bovine (SEQ ID NO:6) (Stumpo et al (1989) *Proc. Natl. Acad. Sci.* USA 86:4012–4016 [as corrected in Seykora et al (1991) *Proc. Nati. Acad. Sci.* USA 88:2505–2509]), murine (SEQ ID NO:7) (Seykora et al, 1991), rat (SEQ ID NO:8) (Erusalimsky et al (1991) *J. Biol. Chem.* 266:7073–7080) and chicken (SEQ ID NO:9) (Graff et al (1989) *Mol. Endocrinol.* 3:1903–1906) MARCKS with that of rabbit (SEQ ID NO:3) and murine MacMARCKS (SEQ ID NO:4). Amino acid identity between all seven sequences is denoted by an asterisk. The conserved charges in the N-terminal, myristoylation domain are indicated with a plus or minus, and the MH2 and effector domains are shadowed. M denotes MARCKS and 42K denotes MacMARCKS.

FIG. 4 shows a comparison of MacMARCKS null and wild type mice. In all panels the MacMARCKS null mice (left) are compared to wild type mice (right).

FIG. 5A is a schematic diagram illustrating neural tube formation in the head region. The stages leading to neural tube formation and closure in wild type mice are illustrated on the right.

An increase in intracellular calcium promotes the binding of calmodulin (Cal) to MARCKS, thereby inhibiting its actin cross-linking activity. This results in a less rigid actin structure, still linked through MARCKS to the membrane (mem actin, hatched). A decrease in intracellular calcium shifts the equilibrium to the resting state, in which MARCKS cross-links actin at the membrane (mem actin, cross hatched). Since calcium levels are known to oscillate following cellular stimulation, MARCKS would mediate cycles of calcium-dependent actin cross-linking activity at the membrane. Upon phosphorylation, MARCKS is unable to bind calmodulin and is released from the membrane, resulting in local destabilization of the actin skeleton (cyt actin, hatched).

FIG. 7 shows that MacMARCKS binds and crosslinks F-actin. MacMARCKS cosedimented with F-actin. 40 $\mu$M actin was polymerized in the presence of 0.2 to 1.6 $\mu$M MacMARCKS (lanes 2–9). MacMARCKS (1.6 $\mu$M) was also incubated in the same buffer without actin, as control (lane 1). F-actin was centrifuged through a sucrose cushion, and the sedimented proteins were analyzed by SDS-PAGE. B. The effector domain peptide of MacMARCKS increased actin crosslinking, as evidence by increased light scattering. Calcium.calmoduliin, and PKC-dependent phosplhorylation, completely abrogated this crosslinking activity.

Figure 8:
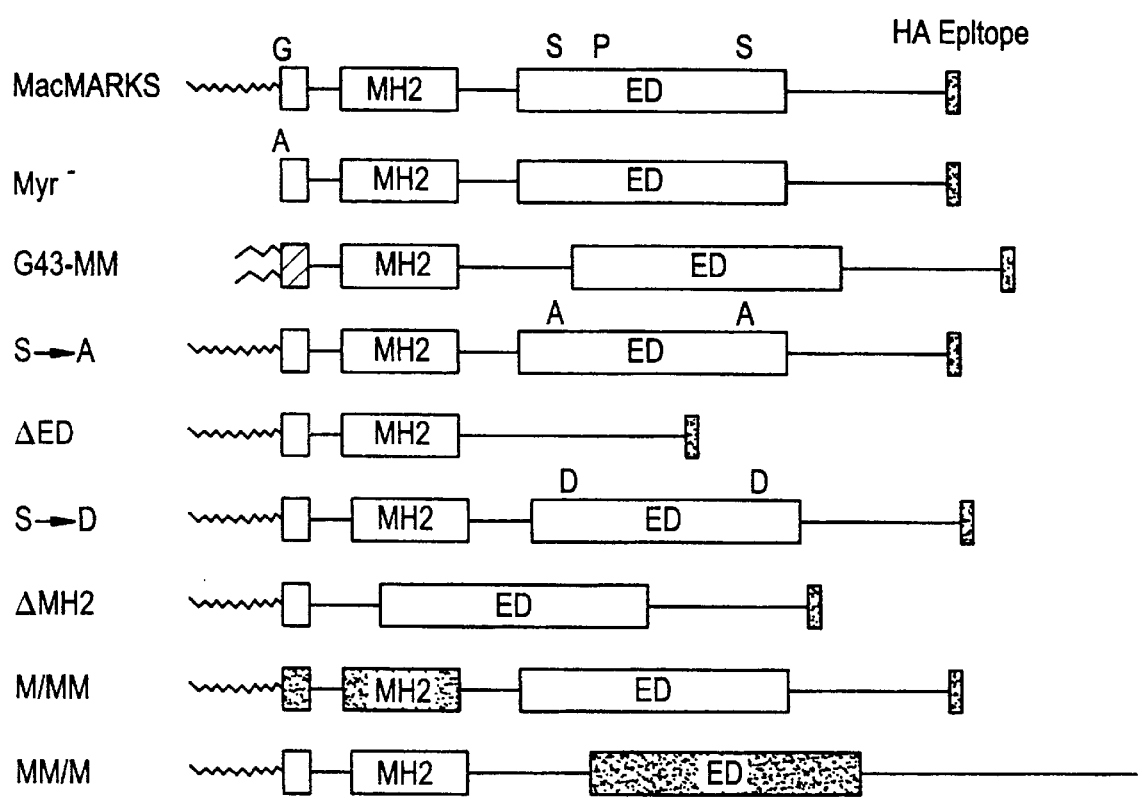

FIG. 8 shows MacMARCKS mutants and chimeras. MacMARCKS is a rod-shaped protein with at least three functional domains; a myristoylated N-terminus, and MH2 domain, and an effector domain (ED), which contains the two serines which are phosphorylated by PKC, as well as the calmodulin and actin binding sites. Wild type MacMARCKS has been HA epitope tagged to allow it to be distinguished form the endogenous molecule. Myr-, the N-terminal myristic acid acceptor glycine (G) has been mutated to alanine (A), thereby preventing myristoylation. G43-MM; is a chimera in which the N-terminus of MacMARCKS has been replaced by the N-terminus of GAP-43. This molecule contains two palmitic acid moieties instead of one myristate. S>A; the serines which are phosphorylated by PKC have been mutated to alanine. ΔED; deletion of the entire effector domain. S>D, the serines normally phosphorylated by PKC have been mutated to aspartic acid to simulate phosphorylation. ΔMH2; deletion of the MH2 domain. M/MM; a chimeric molecule containing the N-terminus and MH2 domain of MARCKS, and the effector domain and C-terminus of MacMARCKS. MM/M; a chimeric molecule containing the N-terminus and MH2 domain of MacMARCKS and the effector domain and C-terminus of MARCKS.

Figure 9A:
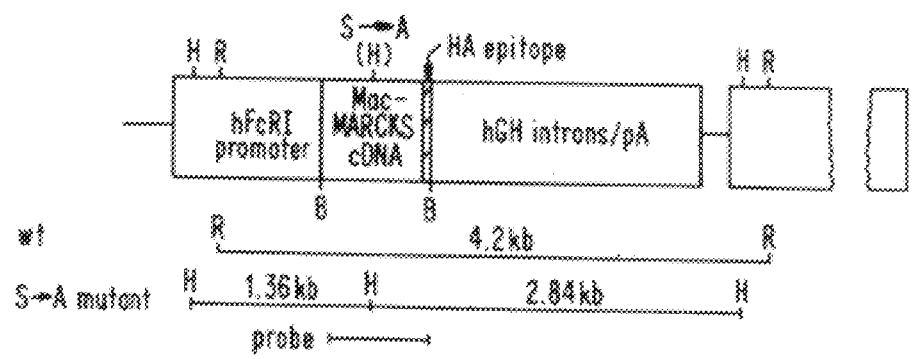
Figure 9B:
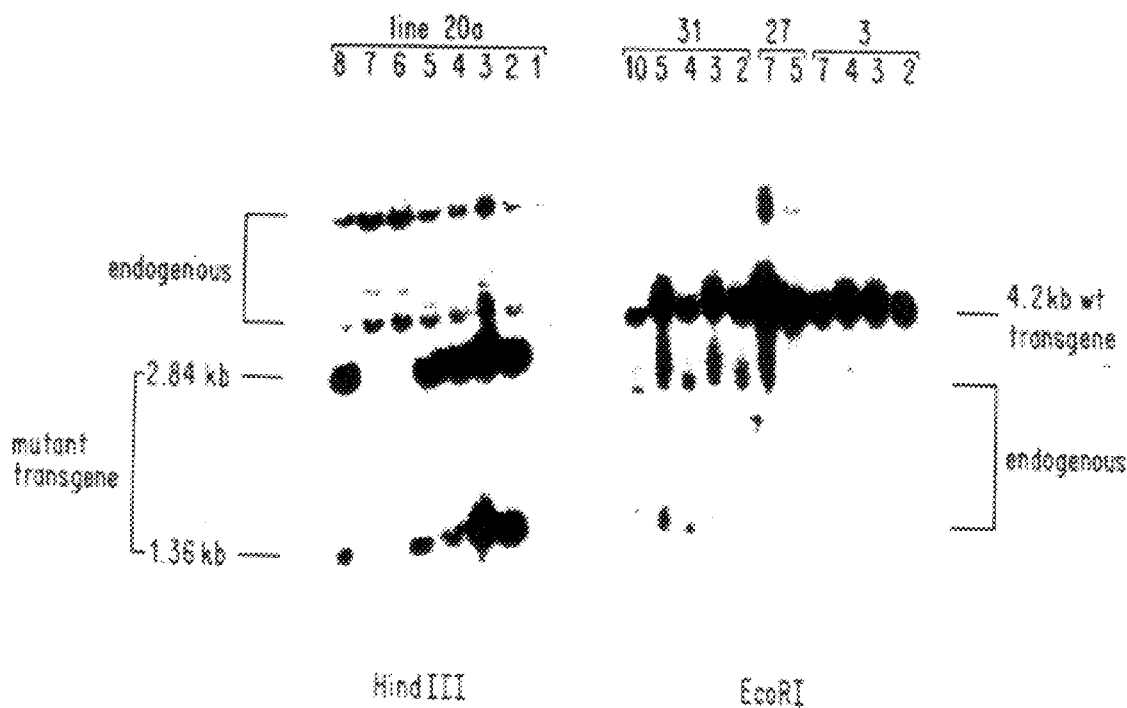

FIG. 9 shows constructs used to generate MacMARCKS transgenic mice and Souther analysis of the transgenic lines. A. The FcγR1-MacMARCKS fusion gene was constructed by cloning the HA-epitope tagged wt or S>A mutant MacMARCKS cDNA into the BamHI site of p1017 vector, and replacing the lck promoter with the 1.1 kb hFcγ1 DNA. Both constructs were sequenced to verify junctional sites. The diagram shows the postulated head to tail multicopy integration of the transgenes into a single site of the mouse genome. Genomic DNA derived from wt MacMARCKS transgenic mice, digested with EcoRI (R) is predicted to yield a 4.2 kb fragment, while genomic DNA from S>A mice, digested with HindIII (H) yield both 1.36 kb and 2.84 kb restriction fragments. B. Southern blot analysis of DNA from transgenic mice harboring hFcγR1-MacMARCKS sequences. Genomic DNA from wt (lines 3, 27 and 31) or the S>A mutant (line 20a) were digested with either EcoRI or HindIII as indicated, and resolved by gel electrophoresis. The DNA was transferred onto nitrocellulose, and probed with a radiolabeled MacMARCKS cDNA probe. The transgenes, as well as the endogenous MacMARCKS sequences, are indicated.

Figure 10:
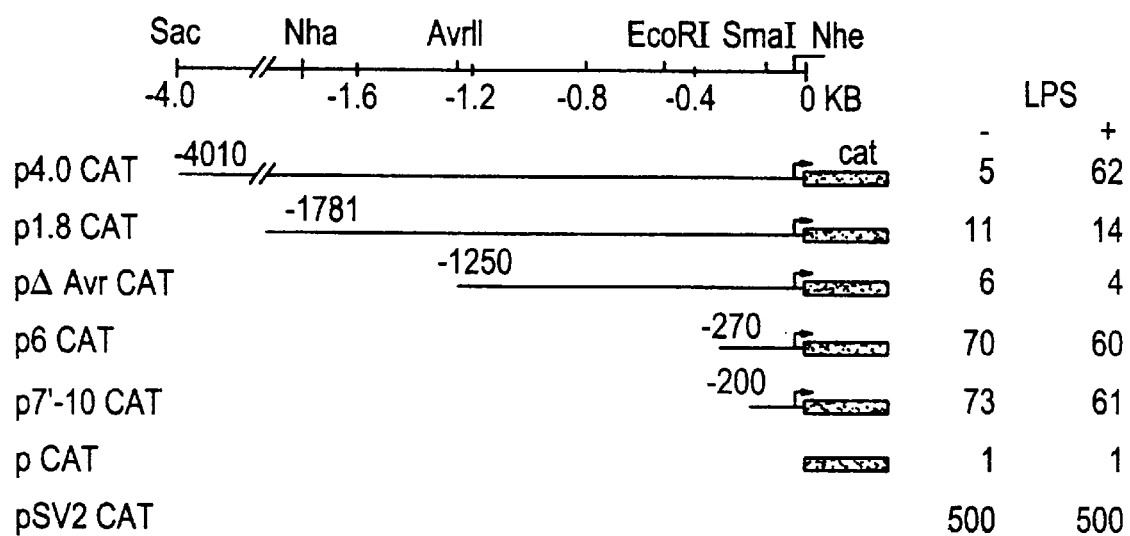

FIG. 10 shows a deletion analysis of the MacMARCKS promoter to define LPS response elements. The 4 kb upstream region, was subcloned into pUCOO-CAT, and deletion clones were generated with the Erase-A-Base system (Promega). Cones containing the indicated lengths of the MacMARCKS upstream sequences were transfected into either CHO-CD14 cells or parental CHO cells by lipofection. In all cases a β-galactosidase construct was cotransfected to serve as a control for transfection efficiency. The cells were either treated in medium alone (−LPS) or medium containing 100 ng/ml LPS (+LPS) for 8 hr. Cell extracts were assayed for both β-gal and CAT activities 48 hr post transfections, and CAT activity was normalized for transfection efficiency and protein concentration. Data is reported as relative CAT activity. Only deletions where major transcriptional transitions occurred are shown.

DETAILED DESCRIPTION OF THE PREFERRED EMBODIMENTS OF THE INVENTION

More particularly, the present invention relates to the discovery that a functional deletion of the MacMARCKS gene causes anencephaly in mice. Because anencephaly is a common human abnormality occurring in 0.1% of pregnancies, the MacMARCKS gene can be used as a diagnostic tool to identify defects in this gene.

MacMARCKS is highly expressed in the developing nervous system (FIG. 4F), implicating the molecule as a signal transducer in mediating anterior neuropore closure. In this model, anencephaly which results in the MacMARCKS null mice appears to be due to defective migration of the neuroepithelium, which prevents closure of the anterior neuropore.

Figure 2B:
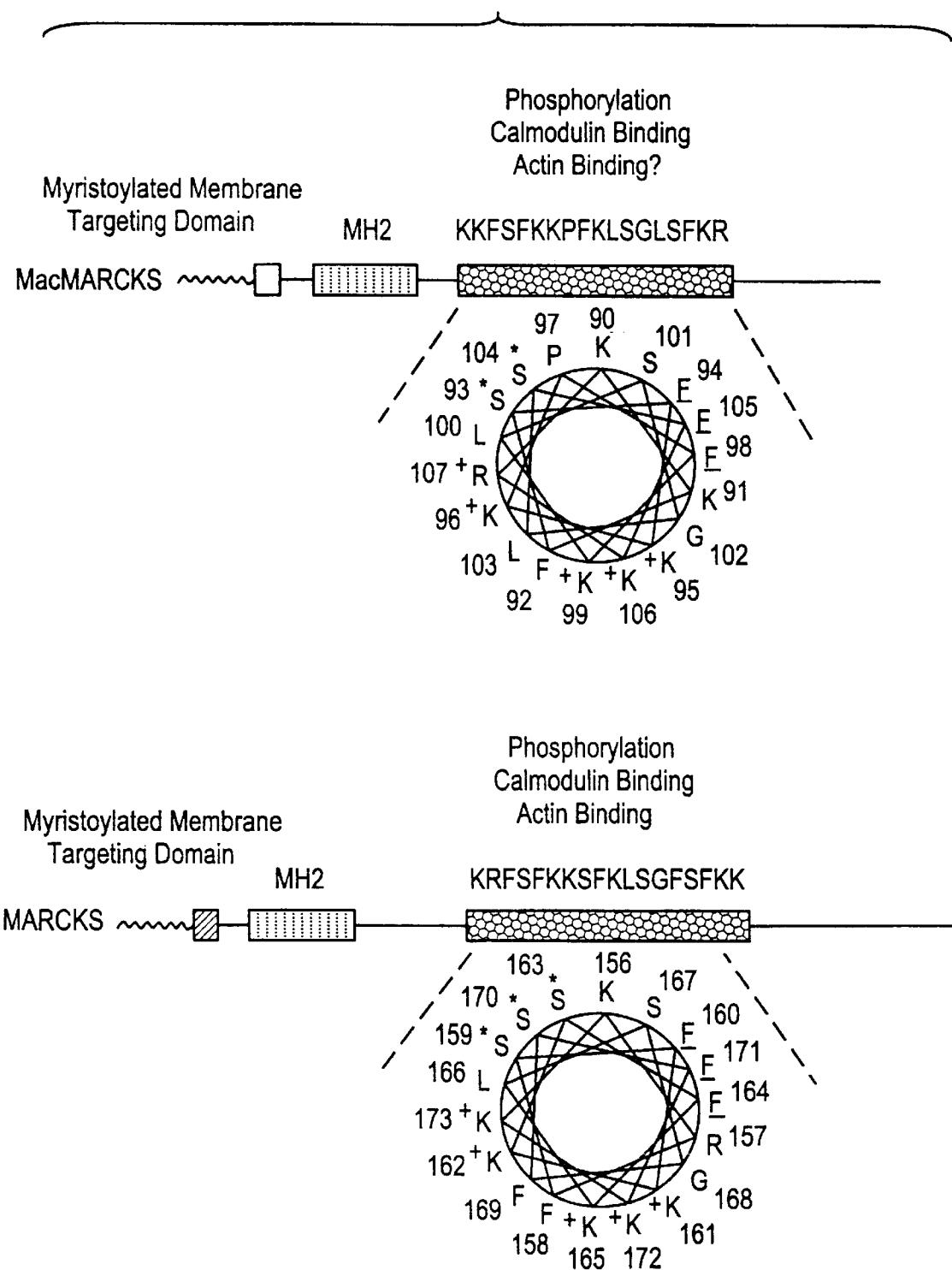
FIG. 2B shows the domain structure of MacMARCKS and MARCKS. The myristoylation, MH2 and effector domains are indicated. The effector domains are also represented as a helical wheel showing the phenylalanine residues that contribute to the amphipathic structure (F), the lysine residues that form the calmodulin and actin binding sites (+), and the serines that are phosphorylated by PKC (*). The numbering of amino acids in the helical wheel is for murine MacMARCKS and MARCKS.
Figure 3:
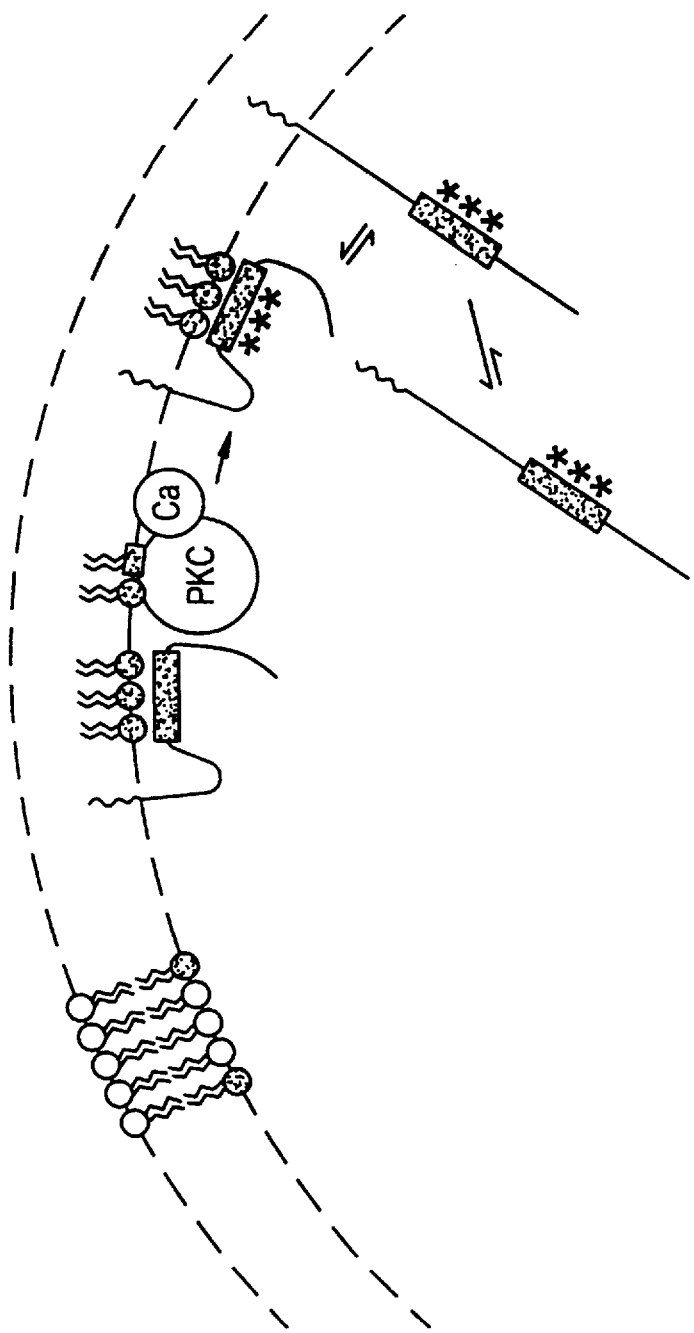
FIG. 3 is a schematic of MARCKS' interaction with the plasma membrane. Going from left to right, MARCKS is shown binding to the plasma membrane by the hydrophobic insertion of its myristoyl chain (wavy line) into the bilayer and the electrostatic interaction between its basic domain (filled rectangles) and acidic lipids (filled circles) on the inner leaflet of the plasma membrane; when the concentrations of diacylglycerol (lipid with a rectangular headgroup) and calcium ions increase, PKC phosphorylates (asterisks) three of the serines in the basic domain of MARCKS. This weakens the electrostatic interaction between the basic domain and the acidic lipids, and the phosplhorylated MARCKS translocates to the cytosol.

The probes of the present invention are derived from the known sequence of the PKC substrate, and particularly from that of MacMARCKS (SEQ ID NOS:3 and 4) or their complements. The entire cDNA sequence of MacMARCKS can be used as a probe for detecting its presence or absence in fetal, amniotic or chorionic cells, but preferably, fragments of the cDNA sequence of the PKC substrate, preferably MacMARCKS, are used. Such fragments can be generated by cleavage with known restriction enzymes, or can be generated using the polymerase chain reaction (PCR). Preferably, the probe is directed to one of the active domains of the PKC substrate, such as the myristoylated membrane targeting domain, the MH2 domain, or the phosphorylation/calmodulin binding/actin binding domain, illustrated in FIG. 2. However, any fragment capable of binding specifically to the PKC substrate can be used.

Because the probe will be used to detect the presence or absence of the gene in cells, a genomic probe or fragment thereof can also be used. In addition, either strand of the cDNA may be used as a probe (i.e., one of the two complementary strands). Moreover, the sequence of the probe need not be identical to the cDNA or genomic sequence, but may have a homology to that sequence sufficient for its specific binding to the gene of interest in the cell. In general, a probe of at least 10–15 nucleotides is preferred. In general, a homology of at least 60%, more preferably 80%, and most preferably 90% is desired. However, those skilled in the art can appreciate that the degree of homology necessary can vary with the particular hybridization conditions used. As temperature and salt concentration decrease, less homology is required. However, those skilled in the art can readily ascertain an appropriate combination of temperature, salt, and homology in order to obtain specific binding The probe can be labelled with any detectable marker known in the art. Such markers include radioactive labels, such as $^{32}P$, $^{35}S$, $^{125}I$, $^{3}H$ and the like. They also include labels such as enzymes which can, in the presence of the appropriate substrate and activator, produce a colorimetric reaction, for example horseradish peroxidase, alkaline phosphatase and the like. The label may also be a biotin entity, which can be used in a sandwich-type assay to bind to labelled avidin, or to avidin and then a labelled anti-avidin antibody. The probe may be labelled with any molecule to which a labelled antibody may then be directed. One example is digoxygenin. Another type of label which may be used is a fluorescent or luminescent molecule, such as fluorescein, rhodamine, Texas Red, AMCA blue, Lucifer yellow and the like.

The probe is preferably used in an in situ hybridization assay to cells of either fetal, amniotic or chorionic origin. Alternatively, the probe could be used to detect the nucleic acid on a Southern-type gel, on which nucleic acid derived from such cells, or amplified from such cells using PCR, is run.

Also contemplated by the invention are PCR probes which can specifically amplify regions of the PKC substrate gene, and be identified on a Southern gel. Such probes are in general at least 10–15 nucleotides in length, and can be directed to amplify regions of particular functional importance in the PKC substrate. Such regions are described above.

Another type of analysis also contemplated by the invention is restriction fragment linked polymorphism (RFLP) analysis. By screening wild-type and mutant populations, differences in restriction fragment patterns can be correlated to mutations in PKC substrates such as MacMARCKS, to detect mutations which may be dangerous or lethal. Such methods are well known in the art.

The present invention also relates to the discovery that the MARCKS and MacMARCKS genes are not redundant, because the MARCKS gene is normal in the MacMARCKS null mice. Thus, these important signalling proteins clearly have different functions.

The present invention also provides homozygous Mac-MARCKS null mice. Although the phenotype is lethal, cells can be successfully generated from mouse embryos for use as diagnostic and analytical tools. In addition, the invention provides macrophages and other hematopoietic cells, including macrophages, obtained from fetal livers of the Mac-MARCKS null anencephalic mice. The invention also provides for epithelial cells lines from MacMARCKS null mice. Additionally, the invention provides a method for repopulating irradiated recipients with MacMARCKS null hematopoietic cells derived from fetal livers of the null mice. An advantage to these repopulated recipients is that they are only MacMARCKS null in their hematopoietic cells, and thus they are a model in vivo system for studying the role of MacMARCKS in immune function. Moreover, they constitute an ideal system for testing therapeutics such as pharmaceuticals and genetic therapy for MacMARCKS-related disorders.

MacMARCKS null mice can be generated by any gene transfer method known in the art. In particular, a protocol especially suited for the present invention is described in *Gene Targeting: A Practical Approach*, A. L. Joyner, ed., IRL Press, 1994, especially at pages 33–61 and 107–146.

The kits provided by the present invention include the probes described above, and can also optionally include a negative control, such as a cell smear on a microscope slide, derived from the anencephalic null mice of the invention. Such cells will demonstrate an absence of the PKC substrate to be detected, such as MacMARCKS, and can be contrasted with cells derived from the sample to be tested.

In the use of the kit of the present invention, a sample would be taken from a patient, in particular from amniotic fluid or chorionic villi, and would be suitably disposed and fixed upon a slide or like substrate. Such samples so fixed could then be detected or observed and compared to the control provided with the kit, as a relatively straightforward means for detecting the presence or absence of the particular protein kinase C substrate. While the method of the present invention extends to both manual and automated practice, as with respect to the latter, suitable equipment may be utilized for the rapid processing and detection of the protein kinase C substrate in samples. In fact, automated sampling devices of this kind are contemplated within the scope of this invention.

The following examples are presented in order to more fully illustrate the preferred embodiments of the invention. They should in no way be construed, however, as limiting the broad scope of the invention.

EXAMPLE 1
Cloning of the rabbit MacMARCKS cDNA

The MacMARCKS gene was isolated from a rabbit alveolar macrophage cDNA library by the method described in Li et al (1992) *Cell* 70:791–801. MacMARCKS was purified to homogeneity from LPS treated rabbit alveolar macrophages. Oligonucleotide probes based on the sequence of tryptic peptides of MacMARCKS were used to screen LPS-induced macrophage cDNA libraries from rabbit and mouse. The full length cDNA from rabbit encodes a 199 amino acid protein with a calculated mass of 19.8 kDa. The murine sequence is 92% identical to the rabbit sequence. MacMARCKS is an acidic, rod-shaped protein with at least three functional domains; a myristoylated N-terminus, an MH2 domain, and an effector domain which contains two serines which are phosphorylated by PKC, and which binds calmodulin and actin. The phosplhorylation sites were defined by peptide mapping and confirmed by mutagenesis.

EXAMPLE 2
Cloning of the murine MacMARCKS gene

The MacMARCKS genomic DNA was cloned by screening a mouse 129sv genomic DNA library (Stratagene, La Jolla, Calif.) using the 5' 200 bp of MacMARCKS cDNA as a probe. The clone (clone 39) containing a 17.8 kb insert was shown to be positive for both 5' and 3' MacMARCKS primers and was mapped in detail with restriction enzymes and used for the construction of the targeting vector.

EXAMPLE 3
Preparation of the targeting vector

The parental vector pPNT was first manipulated to ease the subsequent cloning. The final MacMARCKS targeting construct contained a 7.4 kb 5' SacI genomic fragment as the long arm and a 3' 1.4 kb EcoRI-XbaI fragment as the short arm. To facilitate the easy selection of the embryonic stem (ES) cell clones by Southern blot, a HindIII site was inserted into the SalI site. For the wild type allele, a Southern blot of HindIII digested genomic DNA with the probe A should give a single band of 7.7 kb, whereas the mutant allele undergoing correct homologous recombination should give a shifted band of 4.2 kb. In the final targeting vector pPNT(SH)mm, the GK-TK cassette was kept for the negative selection with the drug FIAU.

EXAMPLE 4
Transfection of the MacMARCKS targeting plasmid

The MacMARCKS targeting plasmid was transfected into J1 ES cells by electroporation and the ES cells were double selected with G418 and FIAU for 7–9 days. The surviving cell colonies were picked, expanded and genotyped by Southern blot.

EXAMPLE 5
Transfer of the MacMARCKS targeting plasmid into mouse blastocysts Five ES cell clones which gave a 4.2 kb band and 7.7 kb band with equal density on Southern blot were injected into 3-day blastocysts of C57/B16 and those blastocysts were transferred into the uterus horn of pseudo-regnant female mice. The chimeric mice were crossed back to C57/B16. ES clone 7 gave germline transmission. Siblings of F1(+/−) were crossed to give C57/B16 mice, with probe A detecting a 7.7 kb HindIII fragment in 129sv mice but a 6.5 kb fragment in C57/B16 mice. 8–10 day old pregnant mice were sacrificed and the embryos were dissected and fixed with fresh 4% paraformaldehyde in PBS at 4° C. for at least two hours. The yolk sac was dissected and used for DNA preparation and the genotyped by PCR.

Figure 4A:
FIGS. 4A and 4B are newly born MacMARCKS null mice which are anencephalic. The skull has not formed and much of the forebrain and midbrain is misplaced or absent. The arrows in A demonstrate the position of the coronal sections shown in FIGS. 4G and 4H.
Figure 4B:
Figure 4C:
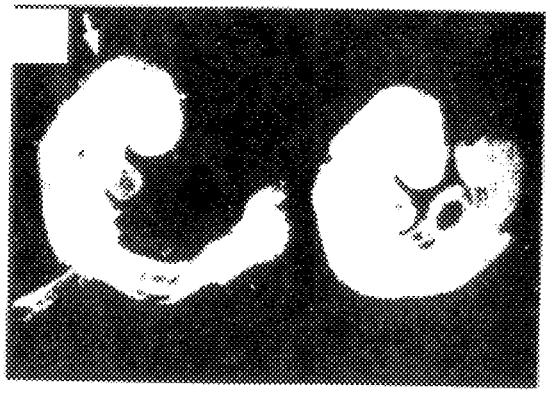
FIGS. 4C–4E show a lateral view of E8.5, 9.5 and 10.5 embryos. Arrows indicate the open anterior neuropore. Arrowheads (E) show the fourth ventricle. The following symbols are used in D; R, rhombencephaloni (hindbrain), M, mesencephalon (midbrain), P, prosencephalon (forebrain).
Figure 4D:

Failure of closure of the anterior neuropore results in MacMARCKS homozygotes being born anencephalic (FIG. 4A, 4B). Comparison of brain development of MacMARCKS mutants versus wild type animals illustrates the sequence of developmental events which results in this mutant phenotype. At E8.5–9.5, in wild type embryos, the neuroepithelial cells of the anterior neuropore proliferate, and undergo extensive migration resulting in closure of the anterior neuropore (FIG. 4C, 4D, right). In MacMARCKS null embryos, while the proliferation of the neuroepithelium is relatively normal, the pattern of cellular migration is altered such that anterior neuropore closure is abrogated (FIG. 4C, 4D, arrow). Specific events marking normal development are: the alar plates close dorsally progressively from the posterior to the anterior neuraxis. By E9.5, the prosencephalon (forebrain), mesencephalon (midbrain), and rhombencephalon (hindbrain) are all clearly visible (FIG. 4D, right).

Figure 4E:
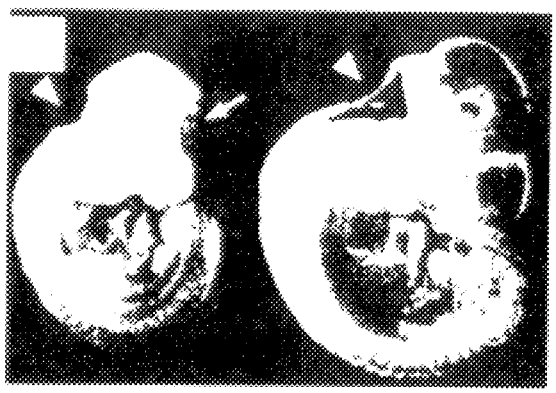
Figure 4F:
FIG. 4F shows in situ hybridization showing MacMARCKS expression in a sagittal section of an E12 embryo. White denotes high expression levels.

In contrast, in MacMARCKS null embryos, the alar plates fail to undergo their convergent migration which normally leads to anterior neuropore closure. This results in the observed malformation of the brain rudiments (FIGS. 4D and 4E, left). In wild type animals, as a consequence of anterior neuropore closure, the non-neural ectoderm which lies lateral to the neural plate before neural tube closure, is brought together dorsally resulting in the formation of the meninges and ectoderm (FIG. 5). The failure of this to occur in MacMARCKS null mutants results in the loss of these structures. This is most readily observed by comparing the area over the fourth ventricle in wild type versus mutant animals (FIG. 4E, arrowheads). Coronal sections of wild type and mutant mice taken in the plane indicated in FIG. 1A of E18.5 embryos demonstrates all the features described above (FIGS. 4G and 4H).

Figure 4G:
FIG. 4G and 4H are 10 micron coronal sections of E18.5 embryos which were stained with hematoxylin and eosin and visualized under 2.5× magnification. The sections were cut rostral of the eye, as shown by the arrows in FIG. 4A. The arrows show the midline. In the wild type mice (H) the neural tube has closed and folded over to form the cortex, the lateral ventricles, the proliferative zone, and the striatum. The meninges and ectoderm (which give rise to the skull) are seen covering the brain. In the MacMARCKS mutant (G), the neural tube has neither closed or folded, and a rudimentary ventricle and cortex are now lateral (extreme left).
Figure 4H:
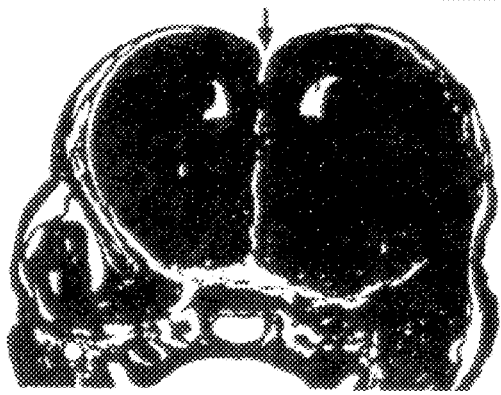
Figure 5B:
FIG. 5B, which should be compared to FIG. 4G, shows the failure of neuropore closure and absence of dorsoventral patterning. The ventricle and the rudimentary cortex are extremely lateral position.
Figure 5C:
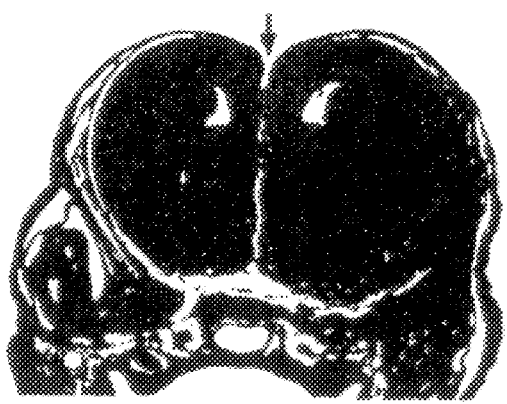
FIG. 5C, which should be directly compared to FIG. 4H, shows the development of anterior structures in an E18.5 wild type mouse. Particularly noteworthy are the closure of the neural tube at the midline (arrow), the ectoderm (which forms the skull), and the position of the cortex and lateral ventricle. In the MacMARCKS null mouse (left), the neural tube fails to close, thereby preventing dorsoventral patterning.
Figure 6:
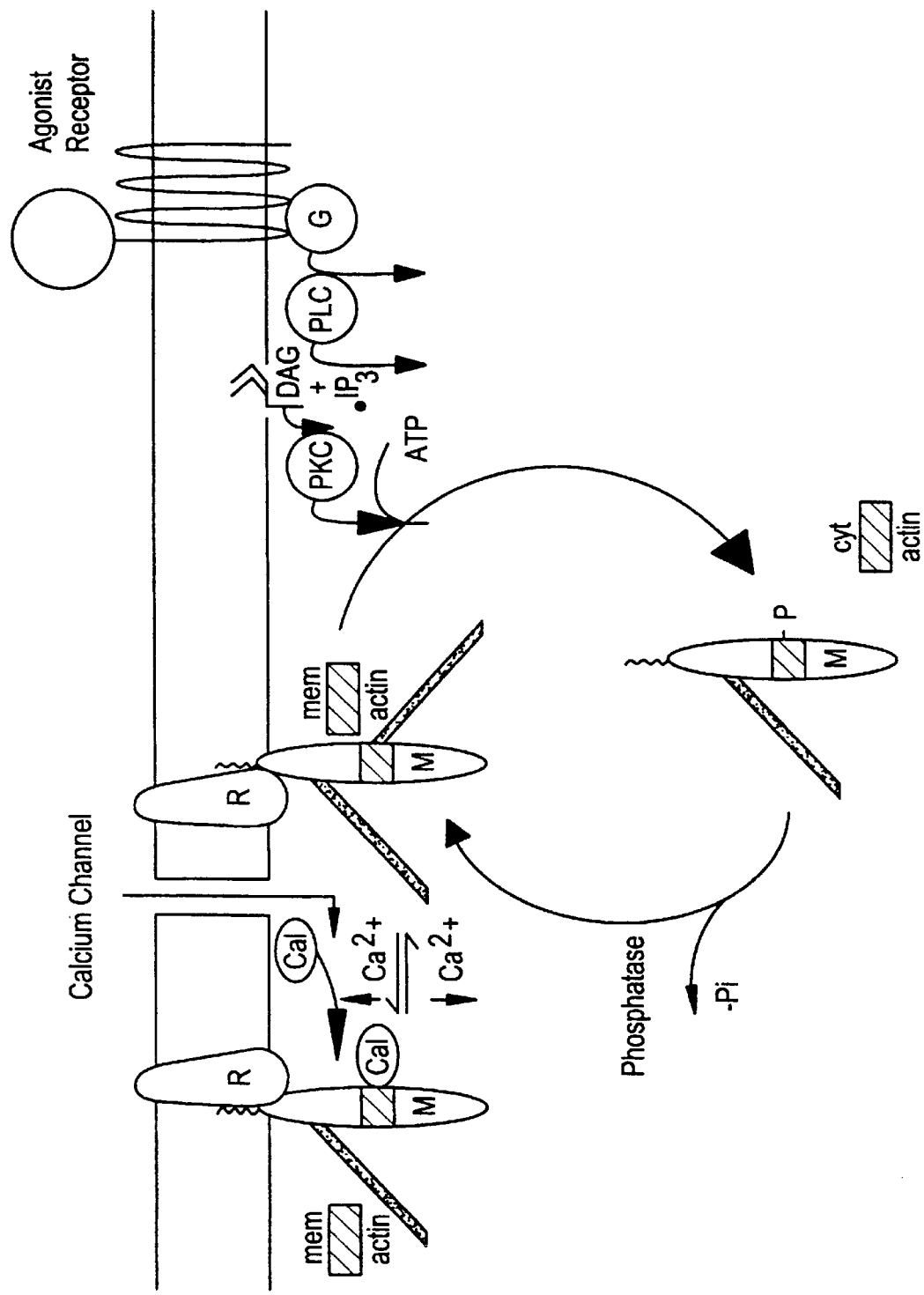
FIG. 6 is a schematic depiction of a mechanism for MARCKS regulation of the actin-membrane interaction. At rest, MARCKS (M) associates with a site on the cytoplasmic face of the membrane, perhaps by binding to a "receptor" (R). In its phosphorylated form MARCKS cross-links actin into a rigid meshwork at the membrane (mem actin, cross-hatched). An agonist receptor activates PKC through a cascade involving G proteins (G) and phospholipase C (P:C). PKC phosphorylates MARCKS, which is released from the membrane. Phosphorylated cytosolic MARCKS remains associated with actin filaments but cannot cross-link actin. The actin linked to phosphorylated MARCKS may be spatially separated from the membrane and more plastic (cyt actin, hatched). When MARCKS is dephosphorylated, it returns to the membrane and again cross-links actin.

In contrast to wild type mice, MacMARCKS null mutants have an open neural plate lacking both overlying ectoderm and meninges (FIGS. 4G and 4H, FIG. 5). The lack of anterior neuropore closure in MacMARCKS mutants is perhaps most readily evident in the position of the cerebral cortex, which lies lateral rather than dorsal to midline structures (FIGS. 4G and 4H). FIG. 5 summarizes the migratory movements of the anterior neurofolds occurring in wild type versus mutant embryos. The combination of normal proliferation and aberrant migratory patterning results in the observed anencephalic phenotype seen at birth. During late embryonic development disruption of the blood brain barrier results in necrosis of the resulting malformed CNS, and this is further exacerbated by the trauma of birth.

EXAMPLE 6

Phosphorylation regulates the binding of MacMARCKS to calmodulin

Purified MacMARCKS bound calmodulin in a calcium-dependent manner, and this association was regulated by PKC-dependent phosphorylation of MacMARCKS. The calinodulin binding domain was defined by mutagenesis, and confirmed by the demonstration that the effector domain peptide of MacMARCKS binds to calmodulin in a calcium-dependent manner. The interaction between the MacMARCKS peptide and calmodulin was also regulated by PKC-dependent phosphorylation of the peptide.

EXAMPLE 7

MacMARCKS is an F-actin crosslinking protein

Figure 7A:
Figure 7B:
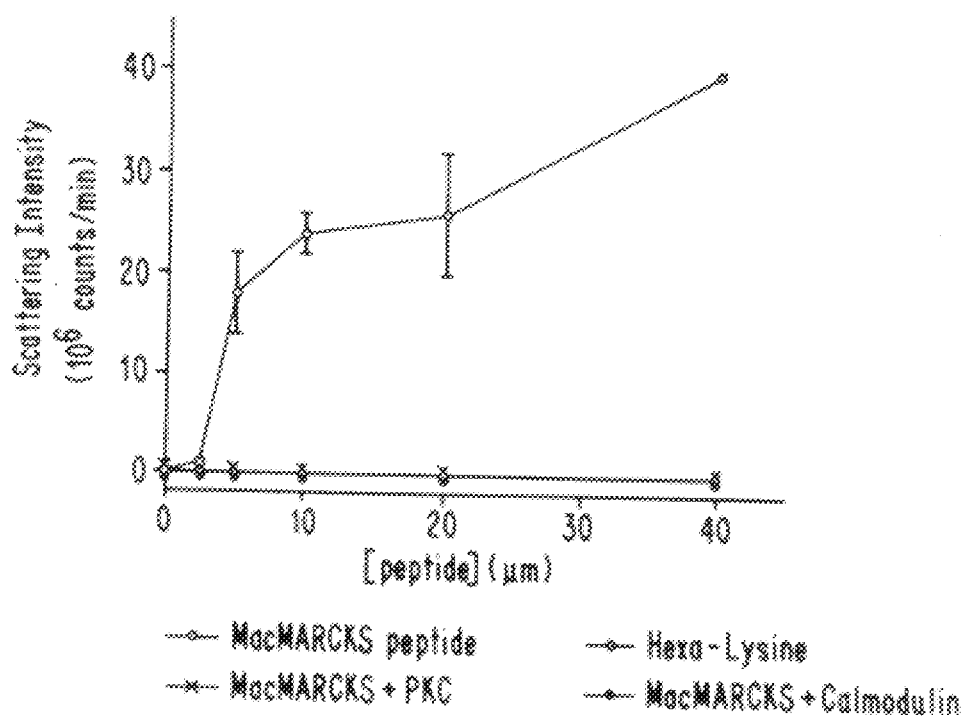

FIG. 7A demonstrates that MacMARCKS binds to F-actin in a specific and saturable manner, with a stoichiometry of approximately MacMARCKS per 12 actin monomers. The apparent Kd is 53 Nm. MacMARCKS also crosslinked F-actin, as evidenced by light scattering end low shear viscosity measurements light scattering experiments also showed that a synthetic peptide based on the effector domain of MacMARCKS crosslinked F-actin (FIG. 7B), and this was confirmed by negative staining and electron microscopy. Phosphorylation of the peptide by purified PKC prevented P-actin crosslinking, as did calcium/calmodulin (FIG. 7B).

EXAMPLE 8

Regulated association of MacMARCKS with phagosomes and endosomes

When macrophages ingest a variety of Gram- bacteria, MacMARCKS associates with the phagosomes containing them. To define when MacMARCKS associates with phagosomes, two markers of phagosome maturation were chosen, actin and Lamp-1. Actin associates with nascent phagosomes, and is depolymerized prior to phagosome-lysosome (PL) fusion, while the lysosomal marker, Lamp-1, only associates with phagosomes after PL fusion. Double staining for actin and MacMARCKS in macrophages which had ingested *S. minnesota* for various times indicated that actin and MacMARCKS coated different phagosomes. A similar experiment demonstrated that MacMARCKS coated the phagosome prior to Lamp-1. The data therefore suggest that MacMARCKS associates with phagosomes after actin depolymerization, but prior to lysosomal fusion.

The mechanism by which MacMARCKS is targeted to maturing phagosomes was further investigated in LPS-treated macrophages ingesting Ig coated magnetic beads. MacMARCKS positive vesicles appear to be recruited to, and rosette the nascent phagosome. These vesicles then appear to fuse with the maturing phagosome after actin is depolymerized. By contrast, the related protein, MARCKS, associates with the phagosome through all phases of maturation. MacMARCKS was highly enriched on purified phagosomes, and this occurred after actin depolymerization.

A clue to the nature of the MacMARCKS coated vesicles was obtained with experiments using aggregated LPS (this effect is observed with concentrations of LPS$\geq$1 $\mu$g/ml). Since light scatter measurements indicate a change in LPS aggregation at this concentration, it is referred to as "aggregated LPS". When macrophages were challenged with aggregated LPS, it was internalized by an endocytic pathway which was indistinguishable from that of acetylated LDL (AcLDL); i.e., LPS and AcLDL were taken up within early endosomes, which fused to form macropinosomes, which ultimately condensed and fused with lysosomes. MacMARCKS was highly enriched on membranes at each phase of the endocytic pathway. Interestingly, the uptake of AcLDL in the absence of high concentrations of LPS did not provoke the association of MacMARCKS with the endocytic compartment, even though MacMARCKS was previously induced to maximal levels by low concentrations of LPS (1 ng/ml). Those data suggest that aggregated LPS induce MacMARCKS binding determinants on the endocytic pathway which are not induced by AcLDL alone.

The above data indicate that MacMARCKS was redistributed from the plasma membrane to lysosomes during the internalization of aggregated LPS and that this occurred by its association with the endocytic pathway. Activation of PKC resulted in the phosphorylation of MacMARCKS, and this promoted its return from lysosomes to the plasma membrane. This indicates that the subcellular targeting of MacMARCKS is highly regulated; it is recruited to the endocytic compartment by aggregated LPS, and phosphorylation promotes its redistribution from lysosomes to the plasma membrane. Staurosporine inhibited both the phosphorylation of MacMARCKS, and its redistribution from lysosomes to the plasma membrane of LPS treated macrophages. In addition MacMARCKS returned to LPS-containing lysosomes when PKC was down regulated by prolonged exposure to PMA.

The mechanism by which PKC might redistribute MacMARCKS was further probed by examining the subcellular distribution of PKC during this event. Activation of PKC translocated PKC$\alpha$ from a diffuse reticular distribution, to lysosomes. The translocation of PKC$\alpha$ to lysosoines correlated temporally with the dissociation of MacMARCKS from lysosomes. In contrast PKC did not associate with lysosomes after addition of PMA. The data suggest that activation of PKC$\alpha$ results in its translocation to lysosomes where it transiently associates with and phosphorylates MacMARCKS, thereby promoting the redistribution of MacMARCKS to the plasma membrane. This data suggests that specific isozymes of PKC have specific functions, that PKC$\alpha$ has a role in lysosome function, and that PKC$\alpha$ is targeted to a specific location within the cell which influences which substrates are phosphorylated.

EXAMPLE 9

Phagosomes containing virulent *S. typhimurium* are not coated with MacMARCKS

As described above, MacMARCKS associates with tight phagosomes containing Gram- bacteria such as *S. Minnesota* (ATCC 49284) and *E. coli* (K12). By contrast, MacMARCKS does not associate with spacious phagosomes containing virulent *S. typhimurium* (14028s). However, when these virulent bacteria are heat-killed, they are internalized in phagosomes with a tightly apposed membrane, which are coated with MacMARCKS. These data confirm that virulent *S. typhimurium* are internalized into macrophages via spacious phagosomes, and suggest that virulence determinants may modify the association of MacMARCKS with the phagosome. Several PhoP mutants of *S. typhimurium* have been isolated which exhibit altered modes of entry and survival in macrophages.

EXAMPLE 10

MacMARCKS is expressed in epithelial cells and neurons iNitial screens suggested that MacMARCKS was highly restricted in its expression, being mainly enriched in LPS-treated macrophages. However, the development of new probes allowed for more rigorous screening, and this led to the identification of MacMARCKS in epithelial cells and neurons. A common property of macrophages, epithelial cells, and neurons is that they exhibit directed membrane traffic, and data in all three systems suggest a role for MacMARCKS in this process.

Neurons: MacMARCKS has been investigated in both PC12 cells and in rat brain synaptosomes. The protein has similar biochemical characteristics to murine macrophage MacMARCKS; it is a rod-shaped protein with a pi of 4.2, and is phosphorylated on the same two serine residues by PKC. Upon depolarization of PC12 calls, MacMARCKS is rapidly and transiently phosphorylated, and this phosphorylation is $Ca^{2+}$ dependent. Similar data were obtained in purified rat brain synaptosomes (sealed nerve terminals). IF confocal microscopy detects the protein both in the perinuclear region, and in varicosities along neurite processes. These results suggest that MacMARCKS may have a role in neurosecretion.

Epithelial cells: MacMARCKS is expressed endogenously in MDCK epithelial cells, and is phosphorylated upon activation of PKC. In nonpolarized cells, MacMARCKS has a random, vesicular distribution. By contrast, in polarized cells, MacMARCKS stains the basolateral membrane, and an endocytic membrane pool localized below the nucleus. Upon activation of PKC, MacMARCKS is phosphorylated, and translocates from the basolateral membranes to the apical surface, where it stains the microvilli prominently. Cell fractionation studies suggest that MacMARCKS moves between the basolateral and apical surfaces of the cell on intracellular membranes.

EXAMPLE 11

Construction and expression of MacMARCKS mutants

A panel of mutants and chimeric molecules has been constructed to probe structure/function relationships of MacMARCKS. The phosphorylation sites, as well as the calmodulin—and actin binding sites have been defined. The mutants are described in FIG. 8. These constructs have been stably expressed in MDCK cells and transiently expressed in the RAW mouse macrophage-like cell line. MacMARCKS mutants are also stably expressed in RAW cells. All constructs were HA-epitope tagged to allow them to be distinguished from the endogenous molecule. A monoclonal antibody to hemagglutinin was used to immunoprecipitate, immunoblot, and visualize by IF mutant MacMARCKS molecules. The mAb to HA shows some non-specific staining of RAW cells. This problem has been circumvented by the use of an affinity-purified rabbit polyclonal antibody to HA. Initial experiments with cells expressing the mutant constructs have confirmed the PKC phosphorylation sites, and have shown that myristoylation is required for membrane binding.

EXAMPLE 12

Generation of transgenic mice expressing wt and mutant MacMARCKS

Transgenic mice in which wild type or mutant MacMARCKS are overexpressed in the context of a macrophage specific promoter were prepared. The hFcγ receptor I promoter was used, which is macrophage-specific, and importantly, is only induced in the presence of interferon-γ. Thus the transgene should only be induced in mice in the context of an immune response. In addition to the wt MacMARCKS transgene, the S>A mutant was expressed, since the nonphosphorylatable form of MacMARCKS is likely to be a dominant negative inhibitor of MacMARCKS function (by analogy with MARCKs). Several lines of transgenic mice have been established carrying either wt MacMARCKS, or the S>A mutant. Both wt and mutant MacMARCKS cDNA's were HA-epitope tagged, and subcloned into the p1017 vector which contained the 1 ck promoter at the 5' end, and the human growth hormone gene at the 3' end. The 1 ck promoter was replaced with the 1.1 kb human FcγRI promoter which confers macrophage-specific expression of heterologous reporter genes, and is inducible by γ-interferon. These constructs produced MacMARCKS protein in a transient transfection system. The constructs were injected by the Rockefeller transgenic facility into the pronuclei of fertilized FVB/N oocytes and transplanted into pseudopregnant females. Founder transgenic mice were identified by tail tipping and Southern analysis. Seven founders carried the wt MacMARCKS transgene and seven carried the mutant transgene (approx 40% efficiency). Founders were crossed to FVB/N mice to generate lines. A total of 4 lines for the wt, and 4 lines for the mutant were obtained. The transgenes are incorporated in multiple copies (approx. 50) into the genome of all lines.

EXAMPLE 13

Cloning of MacMARCKS genomic DNA and characterization of the MacMARCKS promoter to define LPS response elements A 129sv mouse genomic library in lambda FixII vector was screened with a 120 bp Sac-Pst fragment corresponding to the 5' end of the murine MacMARCKS cDNA. Twenty positive clones were identified upon screening $10^6$ phages; clone 39 contained an 18 kb insert which comprised the entire MacMARCKS gene plus flanking 5' and 3' sequences. The gene contains an 87 bp exon I and an 513 bp exon 11, interrupted by a 784 bp intron. The transcriptional start site was defined by RNase protection, and exactly matched the 5' most nucleotide of the cDNA sequence. The 129sv murine library was chosen because, in addition to defining the LPS response elements in the MacMARCKS promoter, it was desired to generate MacMARCKS null mice. The frequency of homologous recombination decreases precipitously between DNA sequences of different mouse strains, and knockout mice are traditionally generated in a 129sv background.

From clone 39, a 4.0 kb SacI-Nhe fragment of the 5' upstream region was subcloned into a promoterless bacterial chloramphenicol acetyltransferase gene (pUCOO-CAT), and from this clone a series of 5' deletion clones were generated by exonuclease digestion (FIG. 10). These constructs, together with the pSV-3-galactosidase plasmid to serve as a control for transfection efficiency, were transiently cotransfected into either CHO-CD14 cells, or into RAW 264.7 cells. The murine macrophage-like line, RAW 264.7, was selected because MacMARCKS is induced in it by LPS, and because it has been used to define a number of macrophage promoters. The CHO-CD14 cells have been transfected with CD14 and are LPS responsive. Studies were initiated with the CHO-CD14 cells because they can be transfected at high and reproducible frequency, and because they represent an authentic cell type for MacMARCKS expression. A murine tissue screen demonstrated that ovaries express high levels of MacMARCKS. The MacMARCKS promoter contains at least three distinct elements. The p4.0 CAT construct shows strong transcriptional activation by LPS (11 fold) (FIG. 10). Deletion of the putative LPS response element (LRE) renders all the other constructs nonresponsive to LPS. Thus the LRE is localized between −4010 and −1781; this region has been subcloned and further characterization is underway. In contrast, p4.0 CAT did not show LPS induced transcription when transfected into the parental, CD14 negative, CHO cells. This further reinforces the notion that CD14 is an LPS-receptor, and points to the utility of CHO-CD14 cells in defining LREs. Comparison of pΔAvr CAT with p6 CAT demonstrates a 10-fold increase in transcriptional activation as the 5' element to −270 is deleted, suggesting that negative regulatory elements lie between −1250 and −270 (FIG. 10). Transcriptional activation to near maximal levels is conferred by sequences 200 bp upstream of the transcriptional start site (compare p7'-10 CAT vs pCAT, FIG. 10), suggesting that it might contain all the elements essential for the constitutive promoter.

EXAMPLE 14

Deletion analysis of the MacMARCKS promoter to define LPS response elements

The 4 kb SacI-Nhe fragment representing the MacMARCKS 5' upstream region, was subcloned into pUCOO-CAT, and deletion clones were generated with the Erase-A-Base system (Promega). Clones containing the indicated lengths of the MacMARCKS upstream sequences were transfected into either CHO-CD14 cells or parental CHO cells by lipofection. In all cases a β-galactosidase construct was cotransfected to serve as a control for transfection efficiency. The cells were either treated in medium alone (−LPS), or medium containing 100 ng/ml LPS (+LPS) for 8 hr. Cell extracts were assayed for both β-gal and CAT activities 48 hr post transfections, and CAT activity was normalized for transfection efficiency and protein concentration. The data is reported as relative CAT activity. Only deletions where major transcriptional transitions occurred are shown.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method for detecting a genetic defect that leads to anencephaly comprising the steps of:
   (a) hybridizing a detectably labelled nucleic acid probe which specifically hybridizes to a gene encoding a MacMARCKS protein to a cell of fetal, chorionic or amniotic origin under conditions suitable for binding of the probe to the gene; and
   (b) detecting the presence or absence of binding; wherein the absence of binding indicates a genetic defect that leads to anencephaly.

2. A kit for the detection of anencephaly comprising:
   (a) the detectably labelled probe of claim 1; and
   (b) a cell null for the gene of claim 1 to be used as a negative control.

3. The method of claim 1 wherein the probe comprises a nucleic acid encoding SEQ ID NO:3 or SEQ ID NO:4, or a complement to said nucleic acid; wherein the probe specifically hybridizes to the gene encoding a MacMARCKS protein.

4. The method of claim 3 wherein the nucleic acid encoding SEQ ID NO:3 has a nucleotide sequence of SEQ ID NO:10.

5. The method of claim 1 wherein the probe comprises a fragment of a nucleic acid encoding SEQ ID NO:3 or SEQ ID NO:4, or a complement to the fragment; wherein the probe specifically hybridizes to the gene encoding a MacMARCKS protein.

6. The method of claim 5 wherein the nucleic acid encoding SEQ ID NO:3 has a nucleotide sequence of SEQ ID NO:10.

7. The method of claim 1 wherein the probe comprises a sequence homologous to a nucleic acid encoding SEQ ID NO:3 or SEQ ID NO:4, or a complement to said nucleic acid; wherein the probe specifically hybridizes to the gene encoding a MacMARCKS protein.

8. The method of claim 1 wherein the probe comprises a sequence homologous to a fragment of a nucleic acid encoding SEQ ID NO:3 or SEQ ID NO:4, or a complement to the fragment; wherein the probe specifically hybridizes to the gene encoding a MacMARCKS protein.

9. A kit for the detection of anencephaly comprising:
   (a) the detectably labelled probe of claim 3; and
   (b) a cell null for the gene of claim 3 to be used as a negative control.

10. A kit for the detection of anencephaly comprising:
    (a) the detectably labelled probe of claim 4; and
    (b) a cell null for the gene of claim 4 to be used as a negative control.

11. A kit for the detection of anencephaly comprising:
    (a) the detectably labelled probe of claim 5; and
    (b) a cell null for the gene of claim 5 to be used as a negative control.

12. A kit for the detection of anencephaly comprising:
    (a) the detectably labelled probe of claim 6; and
    (b) a cell null for the gene of claim 6 to be used as a negative control.

13. A kit for the detection of anencephaly comprising:
    (a) the detectably labelled probe of claim 7; and
    (b) a cell null for the gene of claim 7 to be used as a negative control.

14. A kit for the detection of anencephaly comprising:
    (a) the detectably labelled probe of claim 8; and
    (b) a cell null for the gene of claim 8 to be used as a negative control.

* * * * *